(12) United States Patent
Yu et al.

(10) Patent No.: US 9,710,908 B2
(45) Date of Patent: Jul. 18, 2017

(54) METHOD AND SYSTEM FOR ASSESSING FIBROSIS IN A TISSUE

(71) Applicant: AGENCY FOR SCIENCE, TECHNOLOGY AND RESEARCH, Singapore (SG)

(72) Inventors: Hanry Yu, Singapore (SG); Shuoyu Xu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 35 days.

(21) Appl. No.: 14/759,924

(22) PCT Filed: Jan. 8, 2013

(86) PCT No.: PCT/SG2013/000009
§ 371 (c)(1),
(2) Date: Jul. 8, 2015

(87) PCT Pub. No.: WO2014/109708
PCT Pub. Date: Jul. 17, 2014

(65) Prior Publication Data
US 2015/0339816 A1    Nov. 26, 2015

(51) Int. Cl.
*G06K 9/62* (2006.01)
*G06T 7/00* (2017.01)
(Continued)

(52) U.S. Cl.
CPC ....... *G06T 7/0012* (2013.01); *G01N 33/4833* (2013.01); *G01N 33/576* (2013.01);
(Continued)

(58) Field of Classification Search
None
See application file for complete search history.

(56) References Cited

U.S. PATENT DOCUMENTS

2004/0147840 A1* 7/2004 Duggirala ............... A61B 8/00
                                                                600/437
2013/0030305 A1* 1/2013 Yu ........................ A61B 5/0084
                                                                600/476
(Continued)

FOREIGN PATENT DOCUMENTS

CN    101708123 A    5/2010
CN    102439456 A    5/2012
(Continued)

OTHER PUBLICATIONS

PCT Notification of Transmittal of the International Search Report and the Written Opinion of the International Searching Authority, or the Declaration for PCT Counterpart Application No. PCT/SG2013/000009, 10 pp., (Mar. 18, 2013).
(Continued)

*Primary Examiner* — Jason Heidemann
*Assistant Examiner* — Brian Shin
(74) *Attorney, Agent, or Firm* — Blakely, Sokoloff, Taylor & Zafman LLP

(57) ABSTRACT

A method for assessing fibrosis in a tissue is proposed. The method uses a test image which is an image of the tissue and comprises identifying, from the test image, a portal collagen area, a septal collagen area and a fibrillar collagen area respectively comprising pixels representing portal collagen, septal collagen and fibrillar collagen of the tissue, obtaining quantitative values of one or more features for each identified area based on characteristics of the identified area in the test image and assessing fibrosis using the quantitative values obtained for all the identified areas.

26 Claims, 19 Drawing Sheets

(51) Int. Cl.
| | |
|---|---|
| G06K 9/52 | (2006.01) |
| G01N 33/483 | (2006.01) |
| G06K 9/46 | (2006.01) |
| G01N 33/576 | (2006.01) |
| G06K 9/00 | (2006.01) |
| G06T 7/10 | (2017.01) |
| G06T 7/143 | (2017.01) |
| G06T 7/62 | (2017.01) |
| A61B 5/00 | (2006.01) |

(52) U.S. Cl.
CPC ....... *G06K 9/00147* (2013.01); *G06K 9/4604* (2013.01); *G06K 9/52* (2013.01); *G06K 9/6256* (2013.01); *G06K 9/6267* (2013.01); *G06T 7/10* (2017.01); *G06T 7/143* (2017.01); *G06T 7/62* (2017.01); *A61B 5/0062* (2013.01); *A61B 5/4244* (2013.01); *A61B 2576/00* (2013.01); *G01N 2333/78* (2013.01); *G06T 2207/10056* (2013.01); *G06T 2207/20112* (2013.01); *G06T 2207/30008* (2013.01); *G06T 2207/30024* (2013.01); *G06T 2207/30056* (2013.01)

(56) References Cited

U.S. PATENT DOCUMENTS

| | | | | |
|---|---|---|---|---|
| 2013/0325924 | A1* | 12/2013 | Moshfeghi | H04L 43/0817 709/203 |
| 2014/0024019 | A1* | 1/2014 | Van Dongen | G01N 33/5091 435/5 |

FOREIGN PATENT DOCUMENTS

| | | |
|---|---|---|
| WO | WO 2011/123068 A1 | 10/2011 |
| WO | WO 2012/121594 A1 | 9/2012 |

OTHER PUBLICATIONS

PCT Notification of Transmittal of International Preliminary Report on Patentability (Chapter II of the Patent Cooperation Treaty) for PCT Counterpart Application No. PCT/SG2013/000009, 8 pp., (May 26, 2014).
Shuoyu Xu, et al., "Automated Scoring of Liver Fibrosis through Combined Features from Different Collagen Groups", 33rd Annual International Conference of the IEEE EMBS, pp. 4503-4506, (Aug. 30-Sep. 3, 2011).
Marco Masseroli, et al., "Automatic Quantification of Liver Fibrosis: Design and Validation of a New Image Analysis Method: Comparison with Semi-Quantitative Indexes of Fibrosis", Journal of Hepatology, vol. 32, No. 3, pp. 453-464, (Mar. 2000).
He Yuting, "Liver Fibrosis Surface Assessment based on Non-Linear Optical Microscopy", PhD Thesis, National University of Singapore, 158 pp., (2010).
Raja S. Alomari, et al., "Abnormality Detection in Lumbar Discs from Clinical MR Images with a Probabilistic Model", Proceedings of the 23rd International Congress and Exhibition on Computer Assisted Radiology and Surgery (CARS 2009), 6 pp., (2009).
A. M. Zaitoun, et al., "Quantitative Assessment of Fibrosis and Steatosis in Liver Biopsies from Patients with Chronic Hepatitis C", Journal of Clinical Pathology, vol. 54, No. 6, pp. 461-465, (Jun. 2001).
Ramon Bataller, et al., "Liver Fibrosis", The Journal of Clinical Investigation, vol. 115, No. 2, pp. 209-218, (Feb. 2005).
Scott L. Friedman, "Liver Fibrosis—From Bench to Bedside", Journal of Hepatology, vol. 38, pp. S38-S53, (2003).
Laurent Castéra, et al., "Prospective Comparison of Transient Elastography, Fibrotest, APRI, and Liver Biopsy for the Assessment of Fibrosis in Chronic Hepatitis C", Gastroenterology, vol. 128, pp. 343-350, (2005).
Meng Yin, et al., "Preliminary Assessment of Hepatic Fibrosis with Magnetic Resonance Elastography", Clin. Gastroenterol. Hepatol., vol. 5, No. 10, pp. 1207-1213.e2, (Oct. 2007).
Stella M. Martinez, et al., "Noninvasive Assessment of Liver Fibrosis", Hepatology, vol. 53, No. 1, pp. 325-335, (2011).
Sherif Saadeh, et al., "The Role of Liver Biopsy in Chronic Hepatitis C", Hepatology, vol. 33, No. 1, pp. 196-200, (2001).
Pierre Bedossa, et al., "Liver Biopsy: The Best, Not the Gold Standard", Journal of Hepatology, vol. 50, pp. 1-3, (2009).
Pierre Bedossa, et al., "Intraobserver and Interobserver Variations in Liver Biopsy Interpretation in Patients with Chronic Hepatitis C. The French Metavir Cooperative Study Group", Journal of Hepatology, vol. 20, No. 1, Pt. 1, pp. 15-20, (Jul. 1994).
K. Grønbæk, et al., "Interobserver Variation in Interpretation of Serial Liver Biopsies from Patients with Chronic Hepatitis C", Journal of Viral Hepatitis, vol. 9, No. 6, pp. 443-449, (2002).
Trinidad Caballero, et al., "Liver Fibrosis Assessment with Semiquantitative Indexes and Image Analysis Quantification in Sustained-Responder and Non-Responder Interferon-Treated Patients with Chronic Hepatitis C", Journal of Hepatology, vol. 34, pp. 740-747, (2001).
Zachary D. Goodman, et al., "Progression of Fibrosis in Advanced Chronic Hepatitis C: Evaluation by Morphometric Image Analysis", Hepatology, vol. 45, No. 4, pp. 886-894, (2007).
Vincenza Calvaruso, et al., "Computer-Assisted Image Analysis of Liver Collagen: Relationship to Ishak Scoring and Hepatic Venous Pressure Gradient", Hepatology, vol. 49, No. 4, pp. 1236-1244, (2009).
Zachary D. Goodman, et al., "Fibrosis Progression in Chronic Hepatitis C: Morphometric Image Analysis in the Halt-C Trial", Hepatology, vol. 50, No. 6, pp. 1738-1749, (2009).
Wanxin Sun, et al., "Nonlinear Optical Microscopy: Use of Second Harmonic Generation and Two-Photon Microscopy for Automated Quantitative Liver Fibrosis Studies", Journal of Biomedical Optics, vol. 13, No. 6, pp. 064010-1-064010-7, (Nov./Dec. 2008).
Dean C. S. Tai, et al., "Fibro-C-Index: Comprehensive, Morphology-Based Quantification of Liver Fibrosis using Second Harmonic Generation and Two-Photon Microscopy", Journal of Biomedical Optics, vol. 14, No. 4, pp. 044013-1- 044013-10, (Jul./Aug. 2009).
Luc Gailhouste, et al., "Fibrillar Collagen Scoring by Second Harmonic Microscopy: A New Tool in the Assessment of Liver Fibrosis", Journal of Hepatology, vol. 52, pp. 398-406, (2010).
Warren R. Zipfel, et al., "Nonlinear Magic: Multiphoton Microscopy in the Biosciences", Nature Biotechnology, vol. 21, No. 11, pp. 1369-1377, (Nov. 2003).
Paul J. Campagnola, et al., "Three-Dimensional High-Resolution Second-Harmonic Generation Imaging of Endogenous Structural Proteins in Biological Tissues", Biophysical Journal, vol. 81, pp. 493-508, (Jan. 2002).
Pierre Bedossa, et al., "Sampling Variability of Liver Fibrosis in Chronic Hepatitis C", Hepatology, vol. 38, No. 6, pp. 1449-1457, (2003).
Zachary D. Goodman, "Grading and Staging Systems for Inflammation and Fibrosis in Chronic Liver Diseases", Journal of Hepatology, vol. 47, pp. 598-607, (2007).
R A Standish, et al., "An Appraisal of the Histopathological Assessment of Liver Fibrosis", Gut, vol. 55, pp. 569-578, (2006).
Pierre Bedossa, "Harmony in Liver Fibrosis . . . ", Journal of Hepatology, vol. 52, pp. 313-314, (2010).
Kamal Ishak, et al., "Histological Grading and Staging of Chronic Hepatitis", Journal of Hepatology, vol. 22, No. 6, pp. 696-699, (1995).
Pierre Bedossa, et al., "An Algorithm for the Grading of Activity in Chronic Hepatitis C", Hepatology, vol. 24, No. 2, pp. 289-293, (1996).
Massimo Pinzani, "Liver Fibrosis", Springer Seminars in Immunopathology, vol. 21, No. 4, pp. 475-490, (Jun. 2000).
Evangelos Cholongitas, et al., "A Systematic Review of the Quality of Liver Biopsy Specimens", Am. J. Clin. Pathol., vol. 125, pp. 710-721, (2006).

(56) References Cited

OTHER PUBLICATIONS

Guido Colloredo, et al., "Impact of Liver Biopsy Size on Histological Evaluation of Chronic Viral Hepatitis: The Smaller the Sample, the Milder the Disease", Journal of Hepatology, vol. 39, pp. 239-244, (2003).

Guadalupe Garcia-Tsao, et al., "Now There Are Many (Stages) Where Before There Was One: In Search of a Pathophysiological Classification of Cirrhosis", Hepatology, vol. 51, No. 4, pp. 1445-1449, (2010).

Supatsri Sethasine, et al., "Quantitative Histological-Hemodynamic Correlations in Cirrhosis", Hepatology, vol. 55, No. 4, pp. 1146-1153, (2012).

Chi-Jen Chu, et al., "Detrimental Effects of Nitric Oxide Inhibition on Hepatic Encephalopathy in Rats with Thioacetamide-Induced Fulminant Hepatic Failure: Role of Nitric Oxide Synthase Isoforms", Journal of Gastroenterology and Hepatology, vol. 21, No. 7, pp. 1194-1199, (Jul. 2006).

A. Müller, et al., "Thioacetamide-Induced Cirrhosis-Like Liver Lesions in Rats Usefulness and Reliability of this Animal Model", Experimental Pathology, vol. 34, No. 4, pp. 229-236, (1988).

Tomohiko Akahoshi, et al., "Role of the Spleen in Liver Fibrosis in Rats May Be Mediated by Transforming Growth Factor β-1", Journal of Gastroenterology and Hepatology, vol. 17, No. 1, pp. 59-65, (Jan. 2002).

I. R. Corbin, et al., "Serial Percutaneous Liver Biopsies in Laboratory Rats", Digestive Diseases and Sciences, vol. 48, No. 10, pp. 1939-1943, (Oct. 2003).

Roy Dekel, et al., "Gliotoxin Ameliorates Development of Fibrosis and Cirrhosis in a Thioacetamide Rat Model", Digestive Diseases and Sciences, vol. 48, No. 8, pp. 1642-1647, (Aug. 2003).

Lei Xu, et al., "On Convergence Properties of the EM Algorithm for Gaussian Mixtures", Neural Computation, vol. 8, pp. 129-151, (1996).

C.F.J. Wu, "Jackknife, Bootstrap and Other Resampling Methods in Regression Analysis", The Annals of Statistics, vol. 14, No. 4, pp. 1261-1295, (1986).

Isabelle Guyon, et al., "Gene Selection for Cancer Classification using Support Vector Machines", Machine Learning, vol. 46, pp. 389-422, (2002).

Herve Abdi, et al., "Principal Component Analysis", Wiley Interdisciplinary Reviews: Computational Statistics, vol. 2, pp. 433-459, (2010).

William H. Greene, "21.7.1 The Multinomial Logit Model", Econometric Analysis, Fifth Edition, Prentice Hall, pp. 720-723 (including cover page, title page, table of contents), (1993).

Frank Aurenhammer, "Voronoi Diagrams—A Survey of a Fundamental Geometric Data Structure", ACM Computing Surveys, vol. 23, No. 3, pp. 345-405, (Sep. 1991).

Thomas Abeel, et al., "Robust Biomarker Identification for Cancer Diagnosis with Ensemble Feature Selection Methods", Bioinformatics, vol. 26, No. 3, pp. 392-398, (2010).

Michal Cohen-Naftaly, et al., "Current Status of Novel Antifibrotic Therapies in Patients with Chronic Liver Disease", Therapeutic Advances in Gastroenterology, vol. 4, No. 6, pp. 391-417, (2011).

First Office Action for counterpart Chinese Patent Application No. 2013800738883.5 with English translation, 36 pages.

Kutami R, Girgrah N, Waniess IR, Snidermari K, Wong FS, Sherman M, et al., "The Laennec grading system for assessment of hepatic fibrosis: validation by correlation with wedged hepatic vein pressure and clinical features", Hepatology 2000;32 (Suppl):407A.

\* cited by examiner

| | CPA | Portal-CPA /CPA | Septal-CPA /CPA | Fibrillar CPA /CPA | Portal Thickness (um) | Septal Thickness (um) |
|---|---|---|---|---|---|---|
| 1802 | 20.79% | 44.88% | 34.20% | 0.92% | 32.75 | 18.26 |
| 1804 | 19.32% | 42.33% | 56.42% | 1.26% | 28.44 | 18.61 |
| 1806 | 11.47% | 39.18% | 59.48% | 1.33% | 27.83 | 21.72 |
| Coefficient of Variation (SD/Mean) | 29.13% | 6.77% | 4.68% | 18.84% | 9.03% | 9.76% |

Fig. 18

METHOD AND SYSTEM FOR ASSESSING FIBROSIS IN A TISSUE

CROSS-REFERENCE TO RELATED APPLICATIONS

This patent application is a U.S. National Phase Application under 35 U.S.C. §371 of International Application No. PCT/SG2013/000009, filed Jan. 8, 2013, entitled A METHOD AND SYSTEM FOR ASSESSING FIBROSIS IN A TISSUE.

FIELD OF THE INVENTION

The present invention relates to a method and system for assessing a condition of a tissue, in particular, fibrosis in the tissue.

BACKGROUND OF THE INVENTION

It is often necessary to assess a condition of a patient's tissue for diagnostic purposes or for evaluating the efficacy of a certain treatment on the patient. For instance, it is necessary to assess fibrosis in the livers of patients with chronic liver diseases. This is because liver fibrosis, which is characterized by the excessive accumulation of newly synthesized extracellular matrix in the liver, is the hallmark of most chronic liver diseases. Examples of such chronic liver diseases include chronic hepatitis B and C virus infections, alcoholic liver disease, non-alcoholic steatohepatitis (NASH) and autoimmune liver disease [1, 2]

To assess fibrosis in a tissue of a patient, biopsy (the extraction of a small tissue sample i.e. a biopsy tissue sample from the tissue of the patient) may first be performed, followed by an assessment of fibrosis in the tissue sample. However, since biopsy is an invasive technique, it creates physical discomfort for the patient and carries a certain degree of risk to the patient.

To date, non-invasive fibrosis assessment techniques (e.g. techniques [3]-[7]) have been developed. However, biopsy still remains the gold standard for fibrosis assessment. This is because while information such as inflammatory activity and collagen architecture may be provided via analysis of the tissue sample obtained via biopsy, such information still cannot be obtained via current non-invasive fibrosis assessment techniques. An example of a current non-invasive fibrosis assessment technique is the FibroScan which measures liver stiffness in a patient based on the velocity of a shear wave sent through the patient's liver and uses this measured liver stiffness as an indication of the extent of fibrosis in the patient's liver.

An objective way of assessing fibrosis in a tissue is to view fibrosis as a condition that progresses through many stages and to estimate the stage of fibrosis in the tissue. Currently, morphological approaches for such fibrosis assessments are usually semi-quantitative and rely mostly on user observations of architectural features in biopsy tissue samples. Examples of such approaches include the Metavir and Ishak methods [23-24] used for assessing liver fibrosis. As user observations of the architectural features in biopsy tissue samples are usually highly subjective due to inter- and intra-observer discrepancies [8-9], it is extremely difficult to track fine incremental fibrosis changes in a patient's tissue using the semi-quantitative approaches. Thus, the staging of fibrosis in these approaches is rather crude.

However, even among patients with the same disease at the same stage, there are variations in the clinical and functional states of these patients. Therefore, the ability to detect fine incremental fibrosis changes is important and will be useful in many applications. For example, such ability will be useful in the evaluation of treatment efficacies and justification of treatment strategies, especially with the development of more costly drugs for the treatment of various diseases (e.g. for the arrest/reversal of hepatic fibrosis). The ability to detect incremental fibrosis changes will also be useful for large-cohort hepatic fibrosis studies. Although current large-cohort hepatic fibrosis studies mostly focus on chronic hepatitis B and C, the epidemiologic landscape is changing. With the burgeoning obesity-related problems across the globe, an increasing populace is suffering from the metabolic syndrome which is associated with a liver disease called NASH that causes pericellular/perisinusoidal fibrosis. It would be beneficial to evaluate this liver disease using a large-cohort hepatic fibrosis study as well. Moreover, the concept of the pathogenesis of cirrhosis has evolved greatly in recent years. In particular, the International Liver Pathology Study Group has proposed replacing the term "cirrhosis" with "advanced chronic liver disease" as it recognizes that cirrhosis, which is usually viewed as a single stage (specifically, the last stage) of liver fibrosis, should instead be viewed as a progressive condition that evolves through more than one stage. In particular, it has been observed that as cirrhosis progresses, there is an exponential increase in the amount of fibrosis in the liver. Furthermore, it has been found that regression of cirrhosis with a reversal of fibrosis is possible. Thus, a pathophysiological staging of cirrhosis that incorporates clinical, histological and haemodynamic findings at different stages is preferable over the current one-stage view of cirrhosis.

As compared to semi-quantitative methods, fully quantitative methods rely less on highly subjective user observations and thus, have the potential to monitor finer incremental fibrosis changes over time [21]. Currently, fully quantitative methods quantifying liver histological information for the diagnosis and treatment of chronic-liver-disease (CLD) related fibrosis have been developed. These methods include image-based morphometric analysis methods, many of which require stained biopsy tissue samples. An example of a current image-based morphometric analysis method is the CPA method which uses a single measurement namely, the collagen percentage area (CPA) (i.e. percentage of collagen in the biopsy tissue sample), to assess fibrosis. This measurement is obtained using an acquired image of the tissue sample and is a quantitative measure reflecting the extent of extracellular matrix (ECM) deposition in the tissue [10-13] the tissue sample is obtained from.

Although using the CPA measurement allows the monitoring of fibrosis progression in research and clinical applications [10-13], such a measurement has its limitations. One of the most commonly reported limitations is that the CPA measurement is highly sensitive to the size of the biopsy tissue sample. For example, Paradis et al. [19] found that the coefficient of variation in CPA measurements obtained for 25 mm-long liver biopsy tissue samples is 45% whereas the coefficient of variation in CPA measurements obtained for 15 mm-long liver biopsy tissue samples is 55%.

In addition, it is more accurate to perform histo-pathological assessment of a tissue based on global architectural changes in the tissue than on a single measurement of fibrosis content in the tissue (such as the CPA) [20]. In fact, many of the recent findings have indicated that using the CPA alone to determine pathological scores for fibrosis in a liver biopsy tissue sample does not accurately assess the fibrosis in the sample [20-22]. Features like vascular shunts and liver cell regeneration are also critical for evaluation of advanced chronic liver diseases [22] but information about such features is also not included in the CPA measurement. With the advent of 3D imaging techniques, information about these features can potentially be obtained from 3D visualisation of biopsy tissue samples and an approach that better utilizes such information is desirable.

In view of the above, it will be extremely beneficial to have a robust and fully quantitative approach that can examine architectural changes in a tissue and detect fine incremental fibrosis changes in the tissue.

SUMMARY OF THE INVENTION

The present invention aims to provide a new and useful method for assessing fibrosis in a tissue.

In general terms, the present invention proposes assessing fibrosis in the tissue by identifying different types of collagen areas in the tissue and using one or more features from each of these types of collagen areas. The collagen areas identified and used in the present invention are pathologically relevant i.e. their pattern of changes as fibrosis in the tissue progresses reflects histo-pathological knowledge related to the fibrosis.

Specifically, an aspect of the present invention is a method for assessing fibrosis in a tissue using a test image which is an image of the tissue, wherein the test image comprises a plurality of pixels having respective intensity values and wherein the method comprises:

identifying, from the test image, a portal collagen area, a septal collagen area and a fibrillar collagen area respectively comprising pixels representing portal collagen, septal collagen and fibrillar collagen of the tissue;

obtaining quantitative values of one or more features for each identified area based on characteristics of the identified area in the test image; and assessing fibrosis using the quantitative values obtained for all the identified areas.

The above-mentioned aspect of the present invention may be used in a method of treating a patient having fibrosis. More-specifically, this method of treating the patient may comprise administering antifibrotic therapy based on an assessment of fibrosis in a tissue of the patient, wherein the assessment is obtained using the above-mentioned aspect of the present invention.

The above-mentioned aspect of the present invention may also be used in a method of treating a patient having cirrhosis. More specifically, this method of treating the patient may comprise performing liver transplant on the patient if an assessment of fibrosis in a tissue of the patient obtained with the above-mentioned aspect of the present invention indicates that the patient has decompensated cirrhosis.

The invention may alternatively be expressed as a computer system for performing such a method. This computer system may be integrated with a device, such as an image acquisition device for acquiring images e.g. a second harmonic generation (SHG)/two-photon excitation fluorescence (TPEF) based imaging system, a Subpixel Perspective Sweeping Microscope (SPSM) or other digital scanners. The invention may also be expressed as a computer program product, such as one recorded on a tangible computer medium, containing program instructions operable by a computer system to perform the steps of the method. The computer program product may be installed on a cloud of a cloud computing system and may be configured to run on a remote server.

BRIEF DESCRIPTION OF THE FIGURES

Embodiments of the invention will now be illustrated for the sake of example only with reference to the following drawings, in which:

FIG. 12(a) shows the selection of relevant portal collagen features in the example implementation of FIG. 3, whereas FIGS. 12(b)-(d) show results associated with principal components of the quantitative values of the relevant portal collagen features of FIG. 12(a);

FIG. 13(a) shows the selection of relevant septal collagen features in the example implementation of FIG. 3, whereas FIGS. 13(b)-(d) show results associated with principal components of the quantitative values of the relevant septal collagen features of FIG. 13(a);

FIG. 14(a) shows the selection of relevant fibrillar collagen features in the example implementation of FIG. 3, whereas FIGS. 14(b)-(d) show results associated with principal components of the quantitative values of the relevant fibrillar collagen features of FIG. 14(a);

FIG. 18 shows a comparison between some of the features used in the example implementation of FIG. 3 and the CPA measurement.

DETAILED DESCRIPTION OF THE EMBODIMENTS

Method 100

Figure 1:
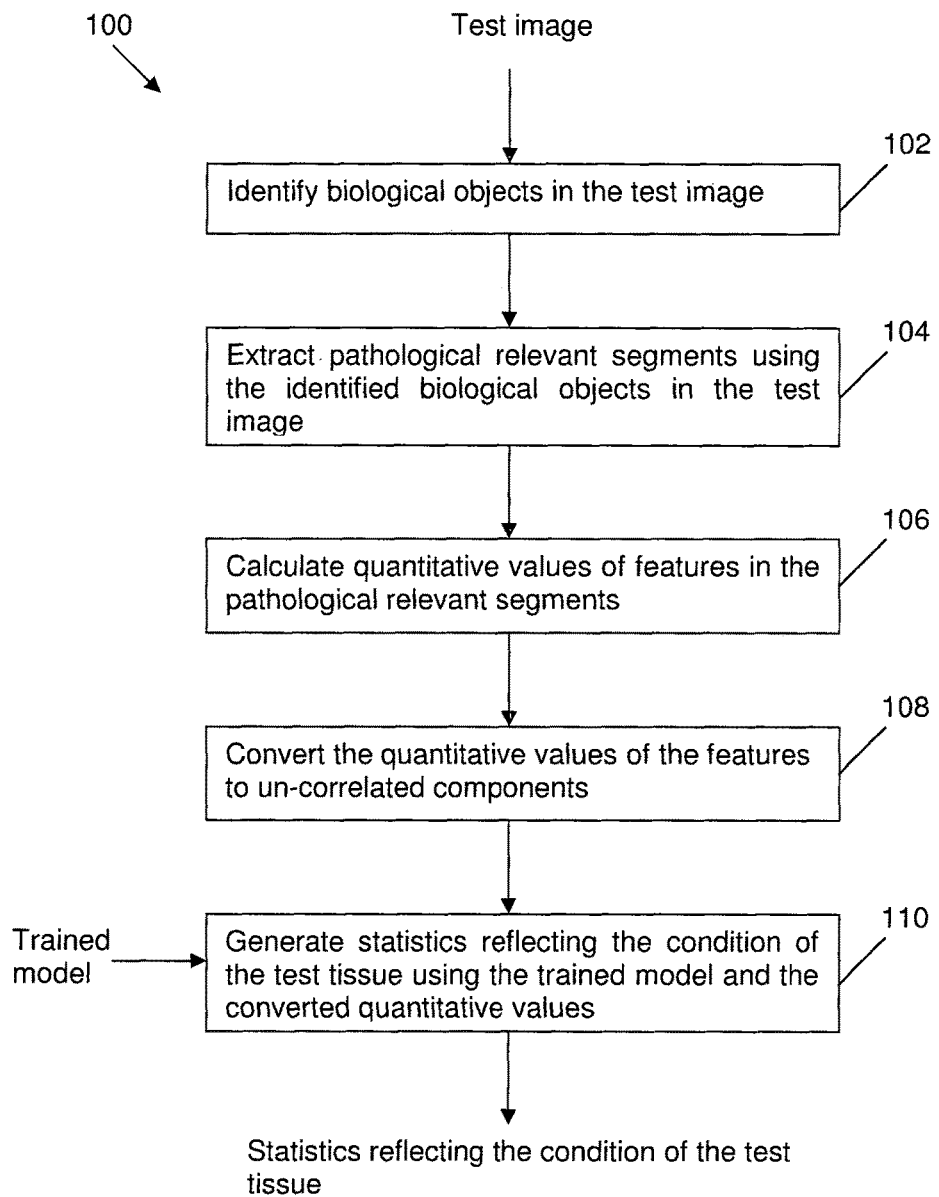
FIG. 1 shows a flow diagram of a method for assessing a condition of a test tissue according to an embodiment of the present invention, wherein the method uses a test image and a trained model.

Referring to FIG. 1, the steps are illustrated of a method 100 which is an embodiment of the present invention and which assesses a condition of a human or animal tissue (test tissue). For example, method 100 may be used to determine a stage of a fibrosis-related disease the test tissue is at. Method 100 may also be used in other applications such as for determining whether the test tissue is cancerous.

The input to method 100 is a test image which is an image of the test tissue. The test image may be an image of a test biopsy tissue sample extracted from the test tissue. Furthermore, the test image may be of any type of image modality. For example, the test image may be obtained using one or more non-linear optics microscopy techniques, such as the two-photon excitation fluorescence (TPEF), the second harmonic generation (SHG), and the coherent anti-stokes Raman scattering (CARS) microscopy techniques. With these non-linear optics microscopy techniques, the test tissue or the test biopsy tissue sample can be directly imaged (i.e. staining of the biopsy tissue sample is not necessary). The test image may also be either a 2-dimensional (2-D) or a 3-dimensional (3D) image, and in the latter case, the 3D test image may comprise a stack of 2D images and method 100 may be performed on each 2D image in the stack independently, with the results for two or more 2D images in the stack being combined to form the overall results.

As shown in FIG. 1, method 100 comprises steps 102-110. In step 102, biological objects are identified in the test image. In step 104, pathological relevant segments are extracted using the identified biological objects. In step 106, quantitative values of features in the pathological relevant segments are calculated. In step 108, the quantitative values are converted to un-correlated components and in step 110, the converted quantitative values and a trained model are used to generate statistics reflecting the condition of the test tissue.

Steps 102-110 will now be described in more detail.

Step 102: Identify Biological Objects in the Test Image

In step 102, biological objects are identified in the test image. These biological objects are objects with a biological meaning. In other words, these objects are expected to be present in the test tissue and whose identification can help in extracting pathological relevant segments later on in step 104. The biological objects identified in step 102 may include cells, nuclei of cells, collagen areas, vessels (or lumens) etc.

Step 104: Extract Pathological Relevant Segments Using the Identified Biological Objects in the Test Image In step 104, pathological relevant segments are extracted using the identified biological objects in the test image. A pathological relevant segment refers to a segment whose pattern of changes reflects histo-pathological knowledge related to the condition method 100 aims to assess.

Histo-pathological knowledge is usually expressed in a qualitative way using descriptive words for use in semi-quantitative scoring systems by pathologists in routine diagnosis of diseases. Thus, prior to performing method 100, an interactive process involving one or more pathologists may be implemented to determine the pathological relevant segments to be extracted. In particular, the interactive process may involve first identifying certain biological objects from one or more images of tissues (of the same type as the test tissue) having varying degrees of the condition method 100 aims to assess, extracting different segments from these one or more images and then having a pathologist verify which of these segments (if any) are pathologically relevant based on his or her histo-pathological knowledge about the condition method 100 aims to assess.

Step 106: Calculate Quantitative Values of Features in the Pathological Relevant Segments In step 106, quantitative values of features in the pathological relevant segments are calculated. To a certain extent, this step can be seen as performing a transformation of the test image into a plurality of quantitative values. The features are also pathologically relevant i.e. their patterns of changes reflect histo-pathological knowledge related to the condition method 100 aims to assess, and may include morphological, texture, co-localization, intensity-based and spatially related features. The quantitative values of these features may be obtained via image processing methods.

Step 108: Convert the Quantitative Values of the Features to Un-correlated Components In step 108, the quantitative values of the features are converted to un-correlated components. The un-correlated components may be in the form of linear combinations of the quantitative values and may reflect the variance in these values.

Step 108 may be done by using transformation techniques such as principal component analysis (PCA), partial least squares (PLS), etc. In some cases, it is possible to select only some (and not all) of the components produced by the transformation technique as the output of step 108. Generally, very few components need to be selected to achieve good results.

Step 110: Generate Statistics Reflecting the Condition of the Test Tissue Using a Trained Model and the Converted Quantitative Values In step 110, statistics reflecting condition of the test tissue are generated using the output of step 108 and a trained model.

The statistics may include one or more indices, probabilities that the test tissue has a particular disease and/or probabilities that the test tissue is at a certain stage of a particular disease. For example, probability values, each indicating the probability that the test tissue is at a particular stage of a disease, may be obtained and from these probability values, an index may be calculated using Equation (1).

$$\text{Index} = \alpha \Sigma p_i * E_i, i = 0, 1, 2, 3, 4 \qquad (1)$$

In Equation (1), $p_i$ is a probability value indicating the probability that the tissue is at stage i of the disease, $E_i$ is the expectation value of the stage i and may be set as i, and $\alpha$ is a scale factor. The summation $\Sigma p_i * E_i$ in Equation (1) converts the probabilities into a continuous measure and the scale factor $\alpha$ serves to normalize this continuous measurement so that the index lies within a desired range. An index may also be calculated using Equation (1) if method 100 aims to determine the tissue type of the test tissue and in this case, $E_i$ may be set as the label of the tissue type used during the training of the model.

The statistics generated in step 110 may be used in several applications. For example, these statistics may be used for diagnosing the patient having the test tissue, for evaluating the efficacy of a certain treatment on the patient and/or for validating other diagnosis tools.

Method 200 for Training the Model

Figure 2:
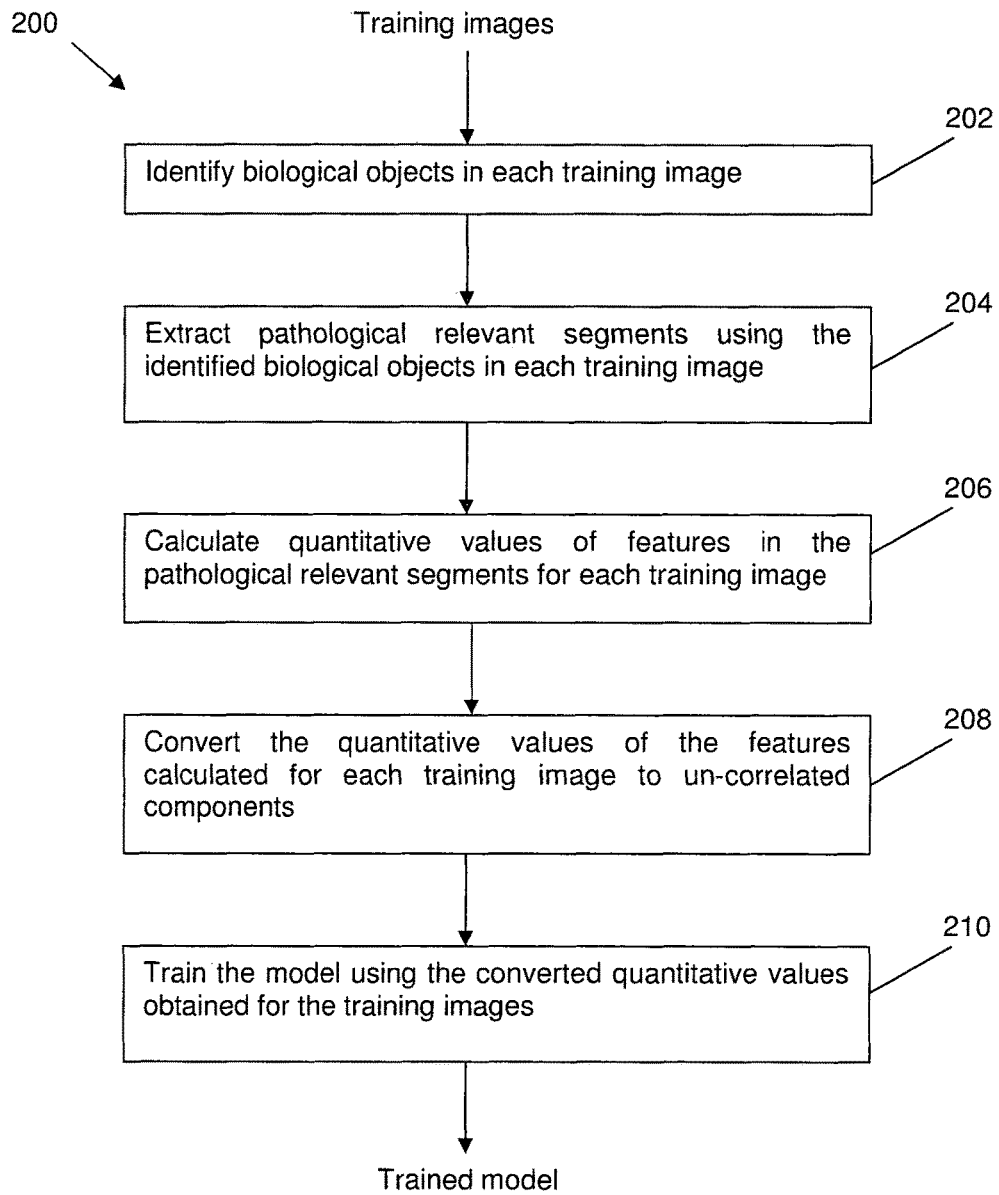
FIG. 2 shows a flow diagram of a method for training the model used in the method of FIG. 1.

FIG. 2 shows a method 200 for training the model used in method 100. The model may be a statistical model or a database, and may use logistic regression, support vector machine, decision trees or artificial neural networks. The model is trained using a plurality of training images obtained by imaging a plurality of training tissues (either directly or by imaging training biopsy tissue samples extracted from the training tissues). Each of these training images has to be associated with known information (or ground truth) about the condition of the respective training tissue. For example, if method 100 aims to determine a pathology score from a certain scoring system (for example, the Metavir system) for the test tissue, then the pathology score of each training tissue has to be known and associated with the respective training image. Similarly, if method 100 aims to determine a label indicating the tissue type of the test tissue, for example, a label '1' indicating that the tissue is cancerous or a label '0' indicating that the tissue is not cancerous, then the label of each training tissue has to be known and associated with the respective training image.

Method 200 comprises steps 202-210. In step 202, biological objects are identified in each training image, in step 204, pathological relevant segments are extracted using the biological objects identified in each training image, in step 206, quantitative values of features in the pathological relevant segments for each training image are calculated, and in step 208, the quantitative values of the features calculated for each training image are converted to un-correlated components. Steps 202-208 of method 200 are similar to steps 102-108 of method 100, except that they are performed on each training image instead of the test image. In step 210, the model is trained using the converted quantitative values obtained for the training images.

Steps 108 and 208 of methods 100 and 200 are optional (even though it is preferable to include these steps because un-correlated components are more appropriate for the statistic learning or training of the model, and including the steps can help reduce the dimension of the quantitative values which can in turn help reduce the computational effort). If steps 108 and 208 are omitted, steps 110 and 210 are performed directly on the quantitative values from steps 106 and 206 respectively. However, note that if step 208 of method 200 is performed while training the model, then step 108 of method 100 must be performed.

Furthermore, in step 206 of method 200, additional steps may be performed to select features relevant to the condition method 100 aims to assess. In particular, the additional steps may include first determining an initial set of features, calculating quantitative values of this initial set of features for the pathological relevant segments of each training image and then selecting relevant features from the initial set of features based on this calculation. The selecting step may be done using a feature selection method according to a pre-defined set of criteria. In this case, only the quantitative values of the relevant features are used in step 208 to train the model. Accordingly, only the quantitative values of the relevant features are obtained in step 106 and used in step 108.

Example Implementation of Method 100 for Assessing Liver Fibrosis

Figure 3:
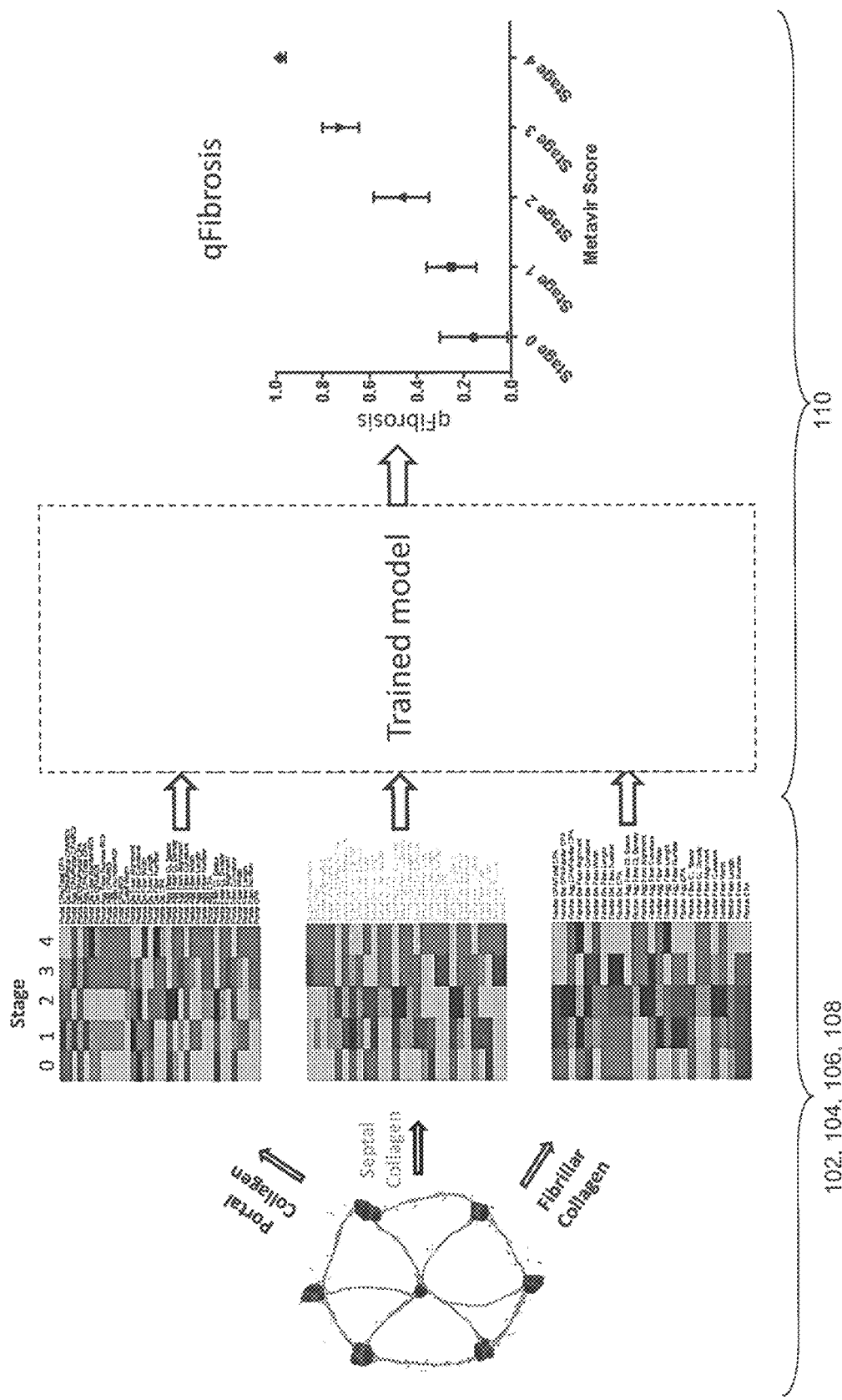
FIG. 3 shows a block diagram of an example implementation of the method of FIG. 1, wherein the example implementation is for assessing liver fibrosis.

FIG. 3 shows a block diagram of an example implementation of method 100 for assessing liver fibrosis. As shown in FIG. 3, in this example, biological objects are identified from the test image to extract pathological relevant segments in the form of three types of collagen areas (a portal collagen area, a septal collagen area, a fibrillar collagen area). The quantitative values of features in these collagen areas are then used with the trained model to produce statistics such as a qFibrosis index. In this example, the model used by method 100 is trained using method 200.

The example implementation of method 100 will now be described in more detail below.

Preparing Test and Training Biopsy Tissue Samples

In this example implementation, TAA-induced rat liver tissue samples were obtained and used. The TAA-induced animal model is a widely used model for studying liver fibrosis in rats. This is because TAA-induced liver fibrosis has similar characteristics as liver fibrosis caused by viral hepatitis [31-32]. Furthermore, humans with liver fibrosis and TAA-induced animals display similar histo-pathological changes. Thus, the TAA-induced animal model is a valid model to study liver fibrosis progression in chronic hepatitis B [33-35].

All protocols for study of the TAA-induced rat model have been reviewed and approved by the Biological Resource Centre (BRC) Institutional Animal Care and Use Committee (IACUC). In particular, male Wistar rats with an average weight of 220 g were housed two per cage in BRC of Biopolis A*STAR with free access to laboratory chow and water in a 12:12 h light/dark schedule. The rats were administrated with intra-peritoneal (ip.) injection of TAA (200 mg/kg of body weight) with PBS, three times a week. Twenty-five rats were randomly separated into five groups. One of the groups was set as a control group in which the rats are not treated with TAA whereas the other 4 groups were associated with time points in the administration of TAA (specifically, the rats in these 4 groups were respectively treated with TAA for 4, 8, 10 and 12 weeks).

A liver tissue sample from the left lateral lobe of each rat was then obtained. Each of these liver tissue samples were preserved in paraffin and sectioned at a thickness of 50 μm for imaging (for the example implementation of method 100) and at 5 μm for staining (for scoring by trained pathologists). The liver histological status of each stained section was assessed by a trained pathologist using the Metavir scoring system which stages liver fibrosis in the section on a scale of F0 to F4. The results of this staging by the trained pathologist are used as the ground truths associated with the rat liver tissue samples.

In this example, method 100 is implemented multiple times, each time using one of the rat liver tissue samples as the test biopsy tissue sample. The trained model used by each implementation of method 100 is trained using the remaining rat liver tissue samples as the training biopsy tissue samples.

Acquiring Test and Training Images

In this example, SHG/TPEF imaging was performed with a 20× objective on the unstained slices of the rat liver tissue samples using the same imaging system as in [14-15]. To cover most of the area in each sample, three nine-by-nine multi-tile images were acquired for the sample, with each of these images having a final image size of 16 mm² (4×4 mm).

Each acquired image is a 2D image comprising data in the SHG channel and data in the TPEF channel. An image having only data in the SHG channel of the acquired image may be referred to as the "SHG image" of the acquired image, whereas an image having only data in the TPEF channel of the acquired image may be referred to as the "TPEF image" of the acquired image. Each of the SHG image and TPEF image of an acquired image comprises a plurality of pixels with respective intensity values, color values and texture values.

Step 102 or Step 202

In this example, the biological objects identified in the test image or in each training image are collagen areas and lumens of the liver tissue sample in the image. This is done as follows.

The collagen areas are identified from the SHG image of the image. This is done using an image segmentation method based on the Gaussian mixture model [36]. More specifically, using the image segmentation method, the pixels of the SHG image are partitioned into collagen pixels (i.e. pixels representing collagen of the liver tissue sample) and background pixels based on their intensity values. Based on this partition, a SHG output mask is produced from the SHG image by giving the collagen pixels a first label and the background pixels a second label.

The lumens are identified from the TPEF image. The TPEF image is used for this purpose because it records the auto-fluorescence signals of the liver tissue sample and thus, the lumens will show up as "empty spaces" in the TPEF image (in other words, the pixels representing lumens in the TPEF image have low intensity values). The identification of the lumens from the TPEF image can thus be done using a segmentation method. In particular, in this example, the pixels in the TPEF image are classified into three groups based on their intensity values by K-means unsupervised clustering and the group of pixels having the lowest average pixel intensity is identified as initial lumen pixels. The areas comprising the initial lumen pixels are then smoothed by applying morphological closing and hole-filling operations to them. The smoothed areas which are small and/or having an irregular shape are then located. In particular, small areas are defined as areas smaller than 100 $\mu m^2$ (assumed to be the largest possible size of one hepatocyte) and areas having an irregular shape are defined as areas with a major-axis-length to minor-axis-length ratio greater than 5 (these areas are assumed to represent sinusoidal spaces). The remaining smoothed areas which are not small and which do not have an irregular shape are then identified as lumen areas. The pixels in these lumen areas are lumen pixels (i.e. pixels representing lumens in the liver tissue sample). In particular, each lumen area represents a lumen in the liver tissue sample. A TPEF output mask is then generated from the TPEF image by giving the lumen pixels in the lumen areas a first label and the remaining pixels a second label.

Next, a combined output mask formed by overlaying the SHG output mask and the TPEF output mask is produced. This combined output mask, together with the SHG output mask and the TPEF output mask are output from step 102 or 202.

Figure 4:
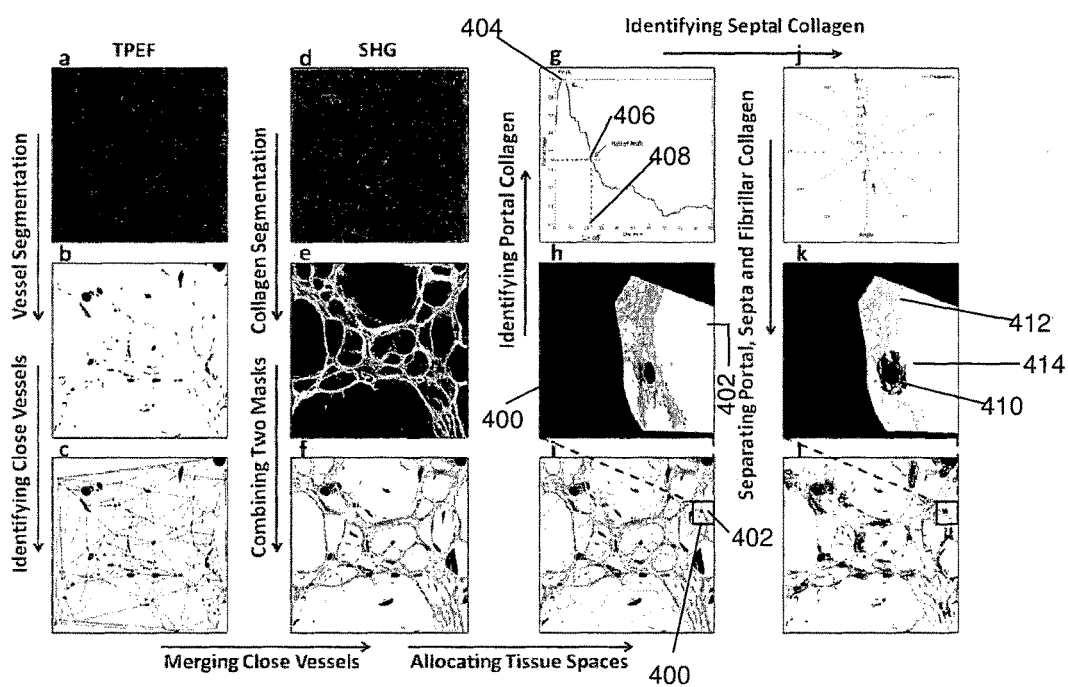
FIGS. 4(a)-(l) show results obtained in the example implementation of FIG. 3 when using a particular acquired image as the test image, wherein these results are obtained from steps used to segment pixels representing collagen in the test image into different types of collagen areas.

FIG. 4(a) shows a TPEF image of one of the images acquired in this example and FIG. 4(d) shows the SHG image of the same acquired image. FIGS. 4(b) and (e) respectively show the TPEF and SHG output masks obtained for the TPEF and SHG images in FIGS. 4(a) and (d). Specifically, the TPEF output mask in FIG. 4(b) shows the lumen pixels in black whereas the SHG output mask in FIG. 4(e) shows the collagen pixels in white.

Step 104 or Step 204

As mentioned above, in this example, the pathological relevant segments extracted in step 104 or step 204 are in the form of three collagen areas, namely a portal collagen area, a septal collagen area and a fibrillar collagen area.

Figure 5:
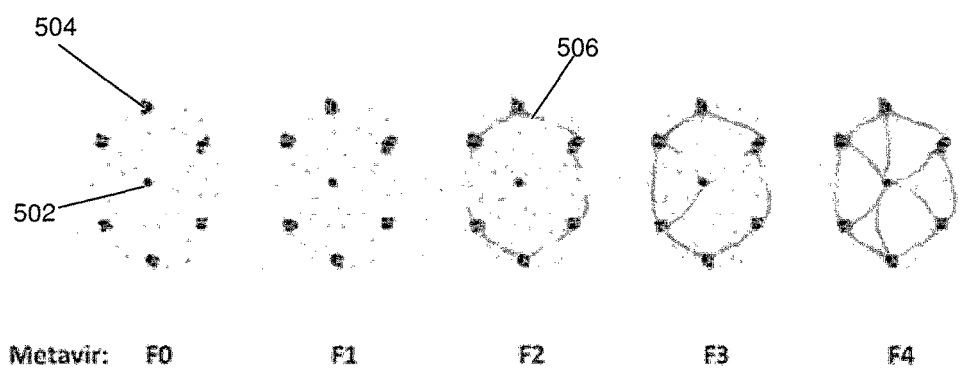
FIG. 5 shows the Metavir scoring system.

Portal, septal and fibrillar collagen architecture patterns of a liver have been verified by pathologists as being strongly indicative of the progression or regression of CLD related fibrosis in the liver. In particular, FIG. 5 shows the Metavir scoring system which is a widely used fibrosis staging system by pathologists and which stages liver fibrosis on a scale of F0 to F4. Based on histo-pathological knowledge in the field of liver fibrosis, it is known that in a normal liver with no fibrosis, the amount of portal collagen which is the collagen around each central vein region (e.g. region 502) and portal tract region (e.g. region 504) is small. A normal liver will be staged at F0 in the Metavir scoring system. In FIG. 5, the portal collagen is shown as black patches around the central vein regions and portal tract regions. In the early progression of fibrosis, portal expansion occurs and each portal tract region in the liver becomes surrounded by more portal collagen. A liver with such portal fibrosis is staged at F1 in the Metavir scoring system. As fibrosis progresses further, spike-like septal collagen (shown as gray lines e.g. line 506 in FIG. 5) starts to grow between some of the portal tract regions in the liver. A liver having such growth is staged at F2 in the Metavir scoring system. With further progression of fibrosis, the septal collagen extends and forms complete bridging between some of the portal tract regions, or between portal tract regions and central vein regions. A liver having numerous septal collagen is staged at F3. The septal collagen eventually extends to form broad complete septa between all of the portal tract regions and central vein regions, intersecting the lobular architecture and surrounding regenerative hepatocellular nodules [20, 23-24], causing the liver to become completely composed of nodules. Such a liver is staged at F4, indicating that the liver has cirrhosis. Changes in the fibrillar collagen close to the sinusoidal spaces in a liver also occur as fibrosis progresses. Fibrillar collagen is shown as gray specks in the spaces between the portal tract regions and each central vein region.

Figure 6:
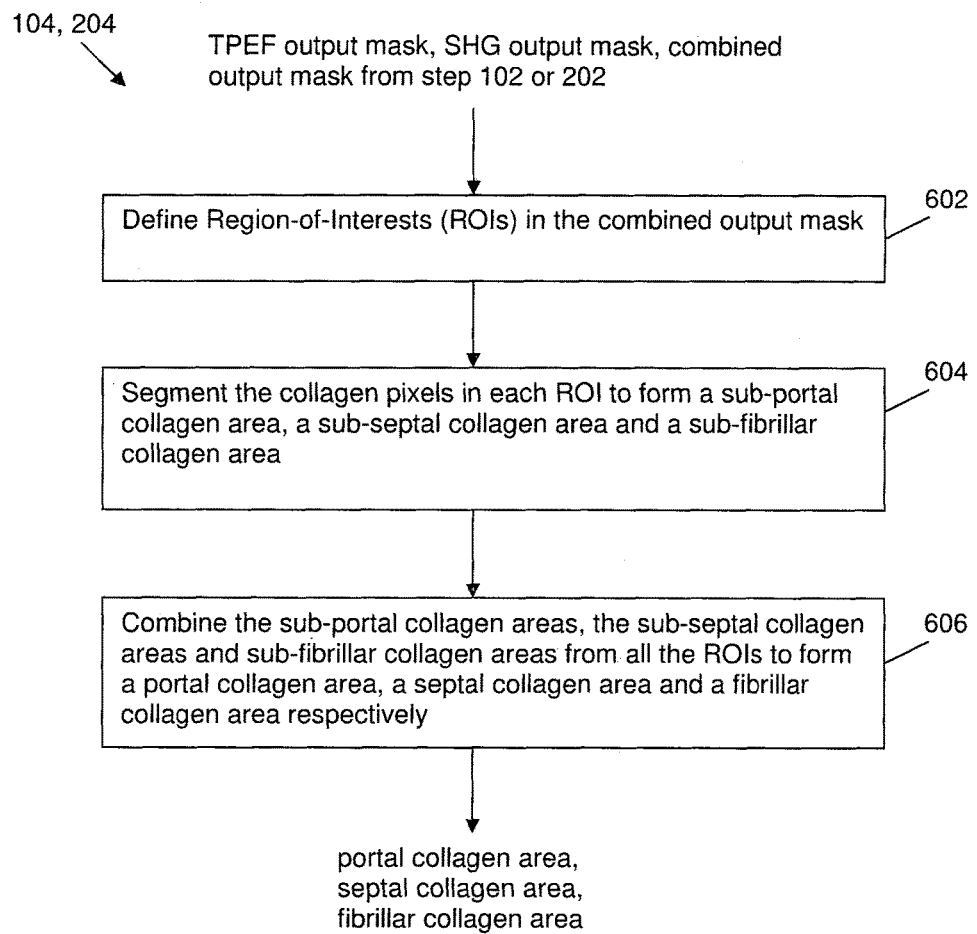
FIG. 6 shows a flow diagram of steps used to segment pixels representing collagen in the test image into different types of collagen areas in the example implementation of FIG. 3.

FIG. 6 shows the sub-steps 602-606 of step 104 or step 204 for extracting the portal, septal and fibrillar collagen areas in an acquired image. These sub-steps 602-606 are elaborated below.

Sub-step 602: Define Region-of-interests (ROIs) in the Combined Output Mask

In sub-step 602, region-of-interests (ROIs) in the combined output mask from step 102 or 202 are defined so that each ROI comprises one portal tract region or central vein region. This is done using the output masks from step 102 or 202.

Theoretically, only three lumens (one hepatic vein, one hepatic artery, and one bile duct) are expected to be present in every portal tract region. However, in practice, there are often more lumens present in one portal tract region due to reasons such as the direction of slicing during tissue sectioning. Therefore, in sub-step 602, the lumen areas in the TPEF output mask are first clustered to form different portal tract regions or central vein regions based on their proximities to one another. This is done using a Delaunay triangulation method. Specifically, a Delaunay triangulation diagram is first generated by treating the centre of each lumen area as a node and then connecting each of these nodes to its immediate neighbouring nodes in a manner such that a plurality of triangles is formed and there is no node inside any of the triangles formed. Small triangles are then identified by applying a threshold length equal to the average length of all the edges of the triangles formed. In particular, a triangle is considered small if it has at least one short edge, that is, an edge shorter than the threshold length. Groups of adjacent nodes connected by the short edges of the small triangles are then identified.

Next, groups of lumen areas in the combined output mask corresponding to the groups of adjacent nodes identified above are picked out. The convex hull of the lumen areas in each of these groups is then identified and filled to form a merged lumen.

The merged lumens, together with the remaining lumen areas in the combined output mask, form a new set of nodes (each merged lumen being a single node). Using this new set of nodes, a Voronoi diagram [42] is created in the combined output mask. A plurality of ROIs are then defined in the combined output mask using the Voronoi diagram such that each ROI comprises one node which is considered to represent a portal tract region or a central vein region.

FIG. 4(c) shows the plurality of triangles formed by performing the Delaunay triangulation method to cluster the lumen areas in the TPEF output mask of FIG. 4(b), whereas FIG. 4(f) shows the combined output mask with the merged lumens (i.e. merged close vessels) formed based on the triangles in FIG. 4(c). FIG. 4(i) shows the Voronoi diagram defined in the combined output mask using the merged lumens and remaining lumen areas in this mask and further highlights a square 400 comprising one of the ROIs (ROI 402) defined using the Voronoi diagram. A magnified view of the square 400 comprising the ROI 402 is shown in FIG. 4(h).

Sub-step 604: Segment the Collagen Pixels in Each ROI to Form a Sub-portal Collagen Area, a Sub-septal Collagen Area and a Sub-fibrillar Collagen Area In sub-step 604, the collagen pixels identified in each ROI are segmented to form a sub-portal collagen area, a sub-septal collagen area and a sub-fibrillar collagen area. This is performed based on relations between the collagen pixels and the lumen pixels (in the node) in each ROI using the steps shown in FIG. 7.

Figure 7:
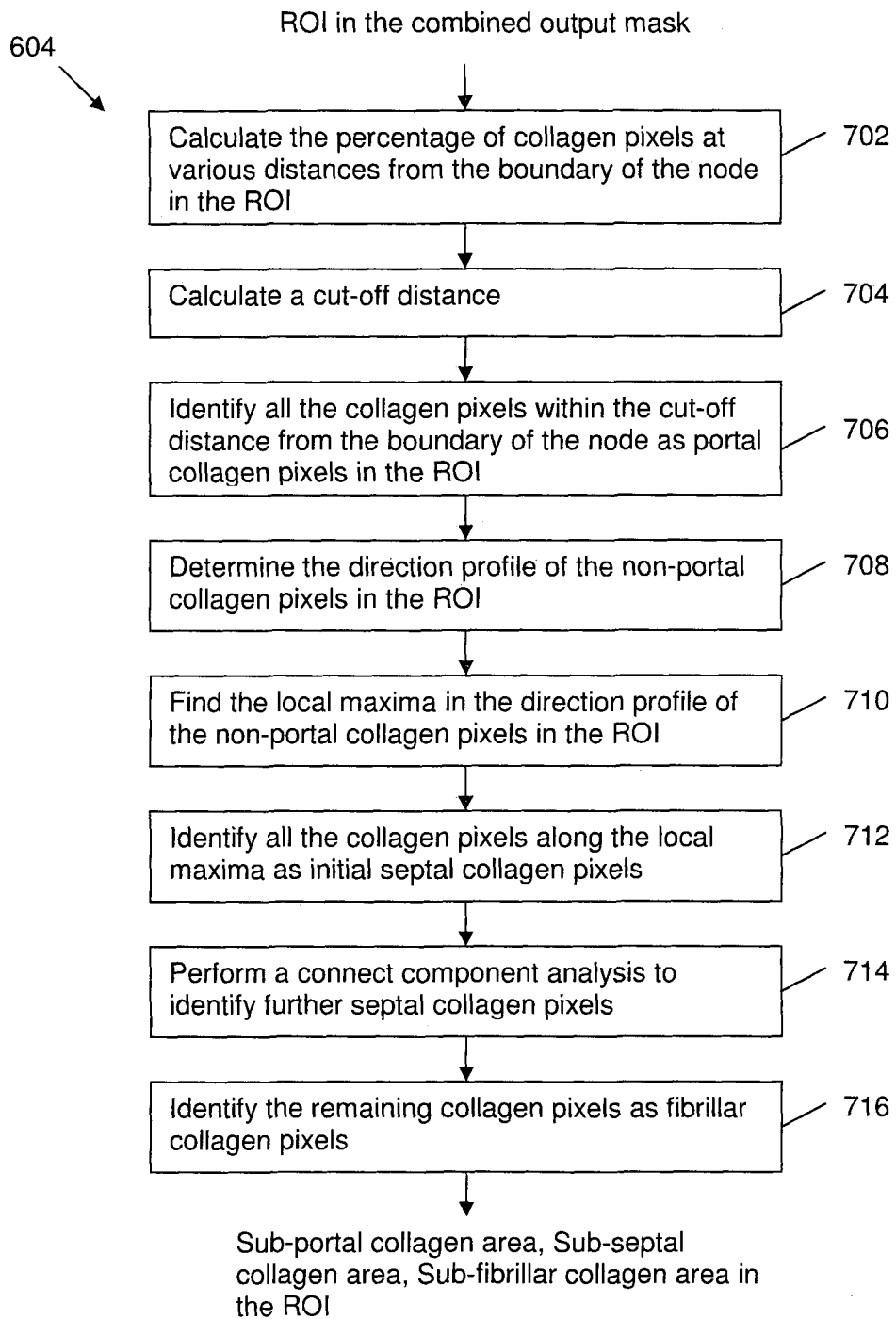
FIG. 7 shows a flow diagram of how a step in FIG. 6 is performed.

In particular, steps 702-706 in FIG. 7 serve to identify the portal collagen pixels (i.e. pixels representing portal collagen) in the ROI.

In step 702, collagen percentages (i.e. percentages of collagen pixels) at a plurality of Euclidean distances from the boundary of the node in the ROI are calculated. Specifically, for each distance in the plurality of distances, pixels at the distance from respective boundary pixels of the node are located and the number of collagen pixels in these located pixels is determined. The collagen percentage for each distance is calculated as the percentage of collagen pixels in the located pixels for the distance.

In step 704, a cut-off distance is calculated as the distance from the boundary of the node at which the percentage of collagen pixels decreases to half of the maximum collagen percentage obtained in step 702.

In step 706, all the collagen pixels within the cut-off distance from the boundary of the node are identified as portal collagen pixels. In other words, the collagen pixels in the pixels located in step 702 for distances below the cut-off distance are identified as portal collagen pixels. These portal collagen pixels form the sub-portal collagen area in the ROI.

Steps 708-714 serve to identify the septal collagen in the ROI.

In step 708, the direction profile of the non-portal collagen pixels (i.e. the collagen pixels not identified as portal collagen pixels) in the ROI is determined. This direction profile comprises direction percentages i.e. percentages of non-portal collagen pixels along different directions from the center of the node in the ROI. Each direction is in the form of a line extending from a center of the node to a pixel in the ROI not comprised in the node (specifically, to a pixel in the boundary of the ROI). The directions are spaced apart by predetermined angles from one another around the center of the node. In the direction profile, the directions are expressed in terms of angles with respect to a reference direction. More specifically, the reference direction is expressed as 0° whereas each of the remaining directions is expressed as the angle between itself and the reference direction). To determine the direction percentage for a direction, the non-portal collagen pixels overlapping with the direction are identified and the direction percentage is calculated as the percentage of non-portal collagen pixels within all pixels overlapping with the direction.

In step 710, the local maxima in the direction profile of the non-portal collagen pixels are found. This is done by first determining for each direction, whether the percentage of non-portal collagen pixels along itself (i.e. whether its direction percentage) is larger than the percentages of non-portal collagen pixels along both its neighbouring directions (i.e. the direction percentages for its neighbouring directions). If so and if the percentage of non-portal collagen along the direction exceeds a predetermined percentage threshold, the direction is considered a local maximum.

In step 712, the collagen pixels overlapping with all the local maxima in the direction profile are identified as initial septal collagen pixels.

Next in step 714, a connect component analysis is performed to identify further septal collagen pixels. In particular, collagen pixels that are not identified as either portal collagen pixels or initial septal collagen pixels are assessed using connect component analysis to see whether they are connected to the initial septal collagen pixels. If any of these collagen pixels is found to connect to an initial septal collagen pixel, this collagen pixel is identified as a further septal collagen pixel. The initial and further septal collagen pixels form the sub-septal collagen area in the ROI.

Finally, step 716 serves to identify fibrillar collagen by identifying all the remaining collagen pixels (i.e. those not identified as either portal collagen pixels, initial septal collagen pixels or further septal collagen pixels) in the ROI as fibrillar collagen pixels representing fibrillar collagen. These fibrillar collagen pixels form the sub-fibrillar collagen area in the ROI.

FIG. 4(g) shows a graph plotting the percentage of collagen pixels at various distances from the boundary of the node in the ROI 402 of FIG. 4(h). As shown in FIG. 4(g), the maximum percentage of collagen pixels occurs at point 404 whereas the percentage of collagen pixels decreases to half of the maximum percentage at point 406. Therefore, the cut-off distance is determined as the distance 408 corresponding to the point 406. FIG. 4(k) shows the identification of the portal collagen pixels 410 as the collagen pixels within the cut-off distance 408 from the boundary of the node in the ROI 402.

FIG. 4(j) shows the direction profile obtained for the ROI 402 of FIG. 4(h). This direction profile in FIG. 4(j) comprises percentages of non-portal collagen pixels along 360 different directions, with the directions evenly spaced apart (specifically, by 1 degree) from one another around the node in the ROI 402. The local maxima in this direction profile are indicated by the arrows. FIG. 4(k) shows the septal collagen pixels 412 in the ROI 402. These septal collagen pixels 412 include the initial septal collagen pixels obtained using the direction profile of FIG. 4(j) and further septal collagen pixels obtained using connect component analysis. FIG. 4(k) also shows the fibrillar collagen pixels 414 in the ROI 402 of FIG. 4(h).

Sub-step 606: Combine the Sub-portal Collagen Areas, the Sub-septal Collagen Areas and Sub-fibrillar Collagen Areas from all the ROIs to Form a Portal Collagen Area, a Septal Collagen Area and a Fibrillar Collagen Area Respectively In sub-step 606, the sub-portal collagen areas, the sub-septal collagen areas and sub-fibrillar collagen areas from all the ROIs are combined to form a portal collagen area, a septal collagen area and a fibrillar collagen area respectively In particular, the portal collagen area is formed by labelling all the pixels belonging to the sub-portal collagen areas in the combined output mask with a first label and the remaining pixels with a second label to produce a binary mask. The septal collagen area and fibrillar collagen area are formed in the same manner except that they use the pixels belonging to the sub-septal collagen areas and the pixels belonging to the sub-fibrillar collagen areas respectively. In other words, three binary masks representing the portal collagen area, septal collagen area and fibrillar collagen area are formed in sub-step 606.

Figure 8:
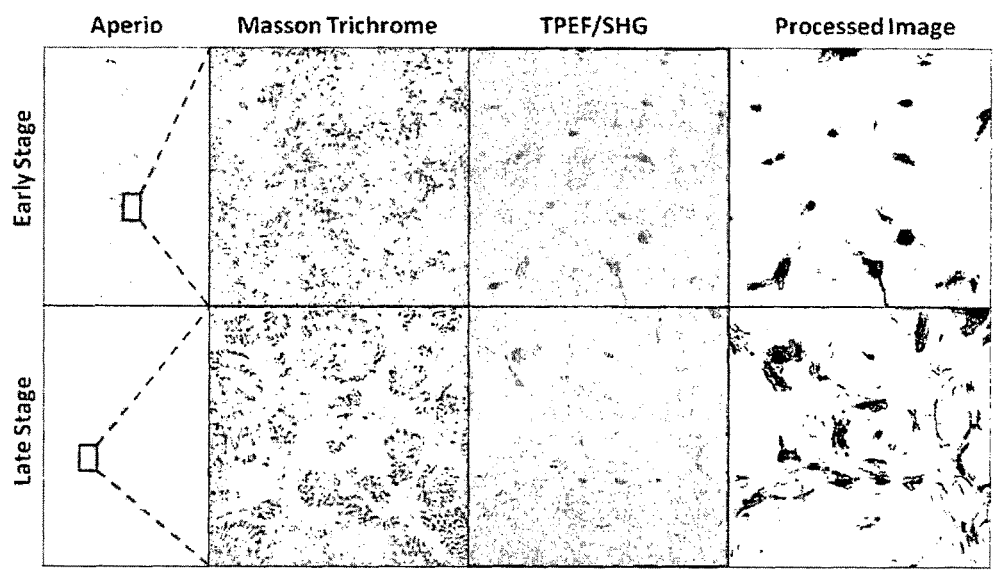
FIG. 8 shows the different types of collagen areas extracted for two tissue samples in the example implementation of FIG. 3.

FIG. 8 shows the portal collagen areas, septal collagen areas and fibrillar collagen areas extracted for two rat liver tissue samples in this example. One of these samples is at an early stage of fibrosis whereas the other one is at a late stage of fibrosis. In particular, each processed image in FIG. 8 is formed by overlaying the binary masks obtained from sub-step 606 for the particular sample and shows the different collagen areas in different shades of gray. It can be seen from these processed images that the different collagen areas are successfully extracted from both tissue samples. In other words, the steps above can effectively extract the different collagen areas in a liver tissue sample regardless of the fibrosis stage of the tissue sample.

Step 206

Figure 9:
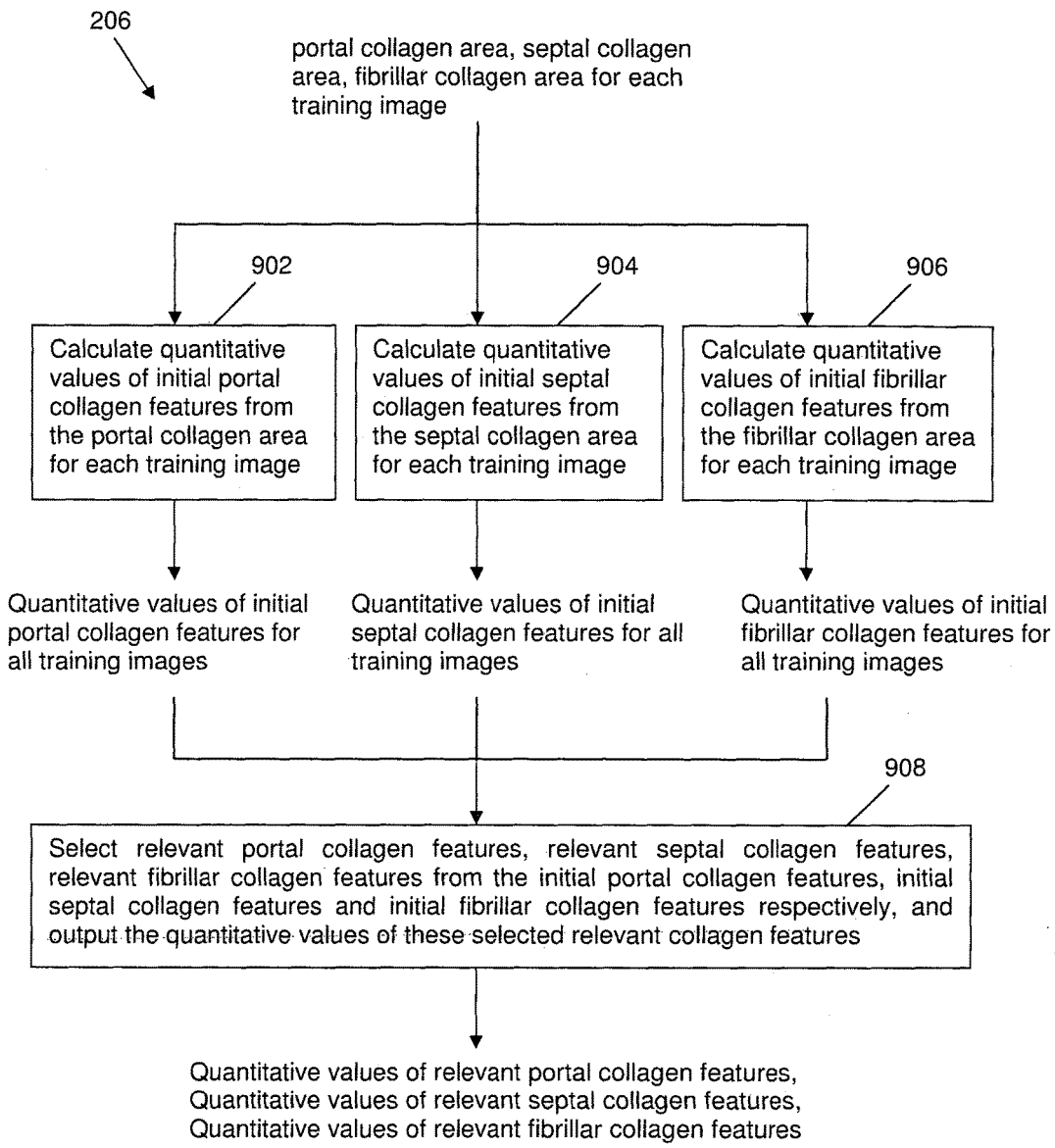
FIG. 9 shows a flow diagram of steps used to obtain quantitative values of features in the different types of collagen areas in the example implementation of FIG. 3.

FIG. 9 illustrates a flowchart showing how step 206 is performed in this example.

In particular, for each training image, quantitative values of initial portal collagen features, initial septal collagen features and initial fibrillar collagen features are first obtained in sub-steps 902-906 using the portal collagen area, the septal collagen area and the fibrillar collagen area extracted in step 204 respectively. Then, in sub-step 908, based on the quantitative values obtained for all the training images, relevant portal collagen features, relevant septal collagen features and relevant fibrillar collagen features are selected from the initial portal collagen features, initial septal collagen features and initial fibrillar collagen features respectively. The quantitative values of these relevant portal collagen features, relevant septal collagen features and relevant fibrillar collagen features for all the training images are then output from sub-step 908 for subsequent use in step 208.

Sub-steps 902-906

Figure 10:
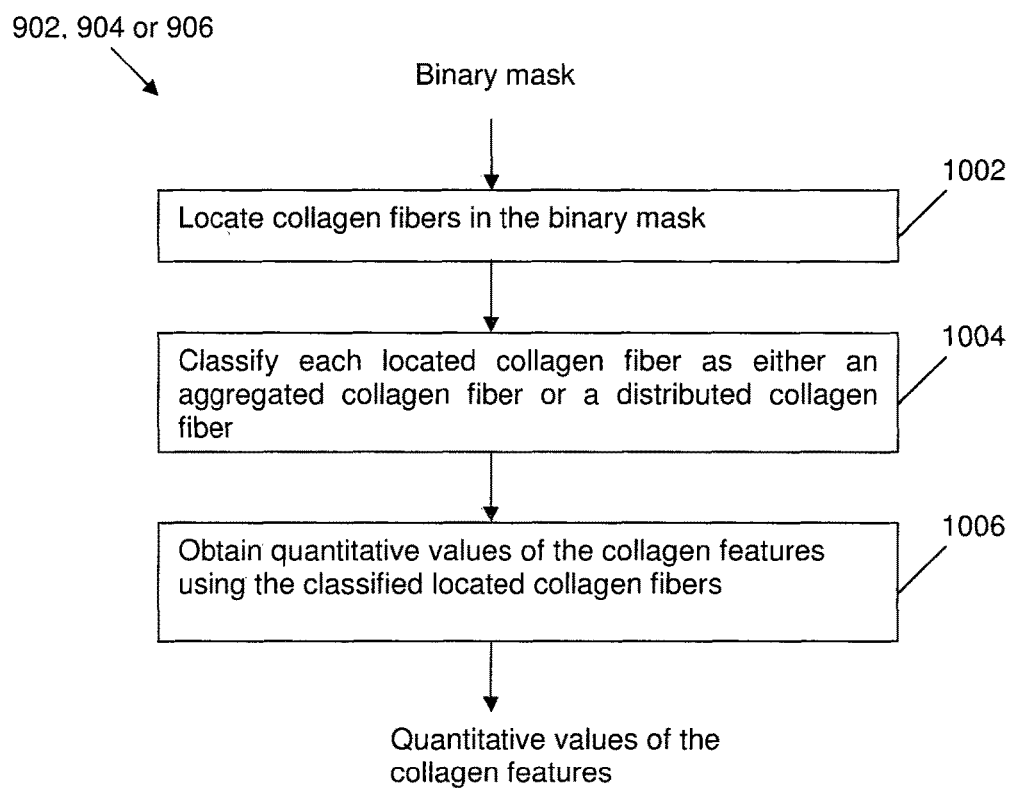
FIG. 10 shows a flow diagram of sub-steps showing how some steps of FIG. 9 are performed.

FIG. 10 illustrates a flowchart showing how each sub-step 902-906 is performed. In particular, the input to each sub-step 902-906 is the respective collagen area obtained from step 204 for the training image, which is in the form of a binary mask comprising a plurality of pixels. As mentioned above, each pixel in each binary mask has either the first label (representing the particular type of collagen in the collagen area) or the second label. In the following description of sub-steps 1002-1006, pixels with the first label in the binary mask are referred to as "target collagen pixels" whereas pixels with the second label are referred to as "non-target collagen pixels".

Sub-step 1002: Locate Collagen Fibers in the Binary Mask

Figure 11:
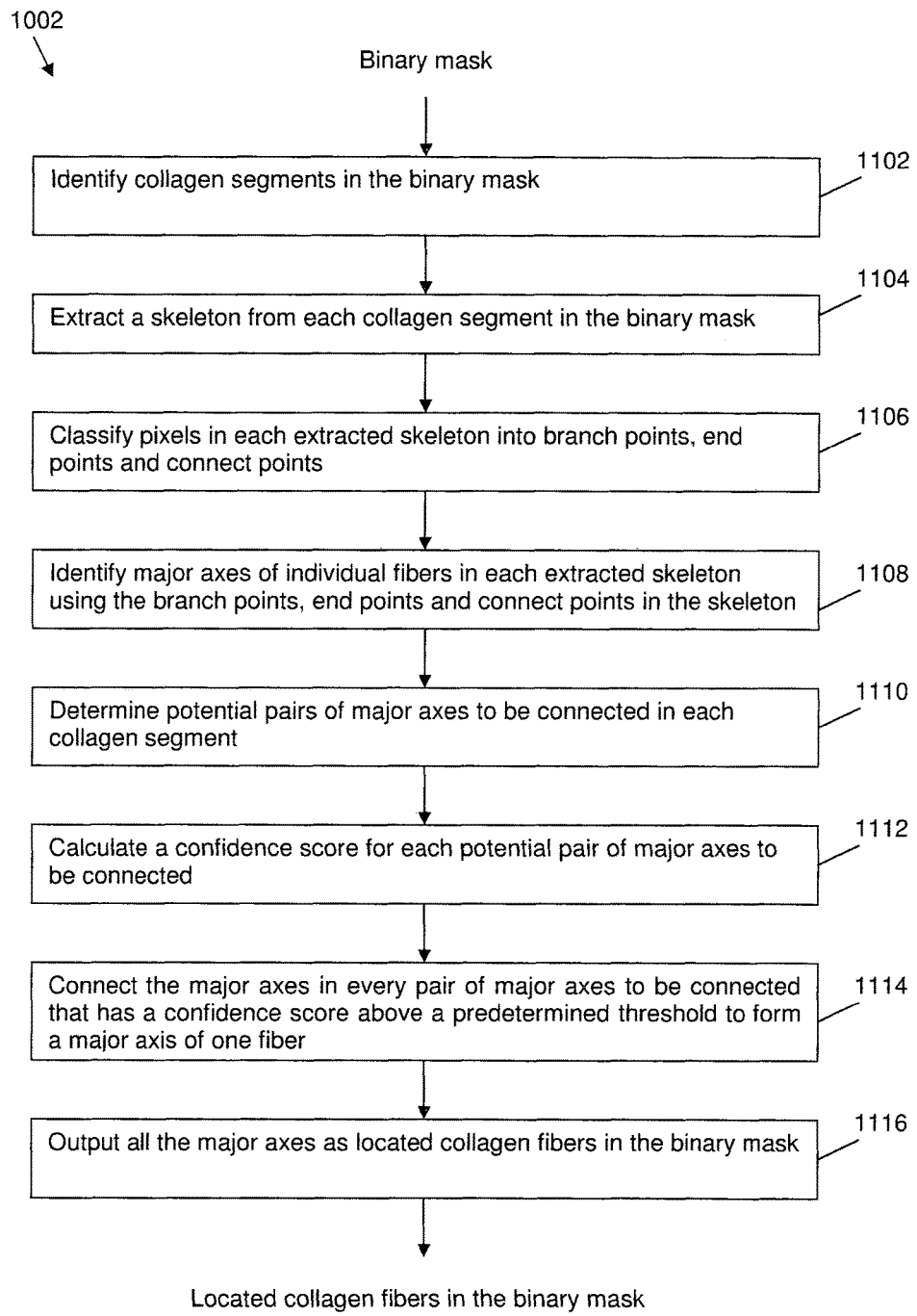
FIG. 11 shows a flow diagram showing how a sub-step of FIG. 10 is performed.

In sub-step 1002, collagen fibers in the binary mask are located whereby each collagen fiber comprises pixels representing a fiber in the liver tissue sample. This is done using steps 1102-1116 as shown in FIG. 11.

First in step 1102, collagen segments in the binary mask are identified by segmenting the target collagen pixels into a plurality of connected components via connect-component analysis. Each connected-component comprises a plurality of connected pixels in the binary mask and is identified as a collagen segment. Each connected component is given a different label (e.g. '1', '2', '3' etc) whereas the non-target collagen pixels are all given the label '0'.

Next, in step 1104, a skeleton is extracted from each collagen segment by thinning the collagen segment using an iterative process as follows. If the collagen segment comprises boundary pixels, an initial skeleton is generated by removing the boundary pixels of the collagen segment. If this initial skeleton also comprises boundary pixels, further skeletons are repeatedly generated by removing the boundary pixels of the most recently generated skeleton. The generation of further skeletons stops when the following stopping condition is valid: the most recently generated skeleton does not comprise boundary pixels. In this document, "boundary pixels" of an object are defined as a set of pixels forming the outline of the object, the outline being an endless loop and enclosing at least one other pixel. The removal of the boundary pixels as mentioned above is performed by morphological erosion. The type of morphological erosion to be used is chosen with the constraint that for all the collagen segments, before the aforementioned stopping condition is valid, removal of the boundary pixels of the most recently generated skeleton will not result in a structure having two or more disconnected groups of pixels i.e. the most recently generated skeleton will not break apart. For each collagen segment, the final skeleton generated in step 1104 for the collagen segment is the skeleton to be output from step 1104. The pixels of each skeleton extracted in the above manner are equidistant to respective boundary pixels of the collagen segment it is extracted from. Furthermore, each skeleton is a good indication of the shape of the collagen segment it is extracted from.

Steps 1106-1108 are then performed to identify individual fibers in each skeleton based on characteristics of the pixels in the skeleton.

In particular, in step 1106, the pixels in each skeleton (i.e. skeleton points) are classified based on whether they represent (a) an end of a fiber in the liver tissue sample, (b) an intersection point between two or more fibers in the liver tissue sample or (c) otherwise. Specifically, a skeleton point is classified as an end point if it represents (a) as mentioned above, a branch point if it represents (b) as mentioned above and a connect point if it represents (c) as mentioned above. The skeleton points are classified as follows. For each skeleton point, if there are more than two skeleton points adjacent to it, the skeleton point is classified as a branch point, if there is only one skeleton point adjacent to it, the skeleton point is classified as an end point and if there are exactly two skeleton points adjacent to it, the skeleton point is classified as a connect point.

Next in step 1108, individual fibers (or more specifically, major axes of the individual fibers) are identified in each skeleton using the branch points, end points and connect points in the skeleton. In particular, for each skeleton extracted in step 1104, a series of searches are performed. Each search starts from an end point of the skeleton and progresses through successive adjacent connect points of the skeleton until a branch point or another end point of the skeleton is reached. If another end point is reached in the search, a major axis of an individual fiber is identified as comprising the points through which the search progressed. If a branch point is reached, the direction of the search path just before reaching the branch point is determined to decide if the search should continue. Specifically, if there is a connect point adjacent to the branch point such that this connect point, the branch point and the connect point immediately before the branch point in the search path form a straight line, the search continues along this straight line through successive adjacent connect points from the branch point. Otherwise, the search stops and a major axis of an individual fiber is identified as comprising the points through which the search progressed. A search in the aforementioned manner is performed for each end point of the skeleton unless the end point has already been identified as part of the major axis of an individual fiber in an earlier search. After all the searches have been performed, the remaining skeleton points are examined to determine if there is any group of connected skeleton points comprising at least one pixel not belonging to any of the identified major axes. If so, each of such groups of skeleton points is identified as a major axis of an individual fiber.

Steps 1110 and 1112 are then performed to locate the collagen fibers in the binary mask based on the major axes in each skeleton identified in step 1108.

In particular, in step 1110, from the major axes of all the skeletons in each collagen segment, potential pairs of major axes to be connected are determined. This is done based on (i) orientations of the pixels in each major axis and (ii) comparisons between the intensity values of a pixel in each major axis and of other pixels in the collagen segment, and is elaborated below. Specifically, since each major axis is formed by the search as mentioned above, each major axis extends from a first terminal point (terminal point 1) to a second terminal point (terminal point 2) with terminal point 1 being an end point classified in step 1106. For each major axis, a direction profile is first created for its terminal point 1 as follows. The direction profile uses a plurality of directions, each comprising a plurality of skeleton points forming a straight line extending from terminal point 1, with the lines spaced apart around terminal point 1. To create the direction profile, for every direction in the aforementioned plurality of directions, a comparison between the intensity values of the skeleton points in the direction and of terminal point 1 is made. Specifically, this comparison is calculated as the ratio of average squared intensity deviation between the skeleton points in the direction and terminal point 1 to the maximum squared intensity deviation between the skeleton points in the direction and terminal point 1. The directions associated with ratios lower than a predetermined threshold of 0.2 are then determined as the local minimum directions. Next, it is determined if there is another major axis whose pixels orientation is close to (i.e. less than 30 degrees from) the orientation of at least one of the local minimum directions. If so, then this other major axis and the major axis are identified as a potential pair of major axes to be connected. Further, a terminal point of this other major axis (in particular, the terminal point nearer to the major axis with the direction profile) and the terminal point 1 of the major axis with the direction profile are identified as potential points to be connected (or potential connecting points).

Next in step 1112, a confidence score is calculated for each potential pair of major axes to be connected based on changes in the intensity values of pixels between the pair of major axes. In particular, step 1112 is performed by first determining a path connecting the potential connecting points for the pair of major axes, and then calculating the confidence score as the sum of entropy of the squared intensity difference between adjacent pixels on this path.

Next in step 1114, the confidence score for each potential pair of major axes to be connected is compared against a predetermined threshold. If this confidence score is above the predetermined threshold, the potential pair of major axes is connected to form the major axis of a single fiber.

Lastly in step 1116, all the major axes are output as the located collagen fibers in the binary mask.

Sub-step 1004: Classify Each Located Collagen Fiber as Either an Aggregated Collagen Fiber or a Distributed Collagen Fiber Next, in sub-step 1004, each collagen fiber located in sub-step 1002 is classified as either an aggregated collagen fiber or a distributed collagen fiber.

In particular, pixels belonging to more than one located collagen fiber in the binary mask are first identified as cross-link points. If a located collagen fiber in the binary mask has one or more cross-link points, this indicates that the fiber links to another fiber and thus, the fiber is classified as an aggregated collagen fiber. Accordingly, the pixels forming this fiber are identified as aggregated collagen pixels (i.e. pixels representing aggregated collagen). On the other hand, located collagen fibers having no cross-link points are classified as distributed collagen fibers and accordingly, pixels forming these fibers are identified as distributed collagen pixels (i.e. pixels representing distributed collagen).

Sub-step 1006: Calculate Quantitative Values of the Collagen Features Using the Classified Located Collagen Fibers Next in sub-step 1006, quantitative values of the initial collagen features are calculated using the classified located collagen fibers.

Sub-step 908: Select Relevant Collagen Features and Output the Quantitative Values of these Selected Relevant Collagen Features In this example, each of the selection of relevant portal collagen features from the initial portal collagen features, selection of relevant septal collagen features from the initial septal collagen features and selection of relevant fibrillar collagen features from the initial fibrillar collagen features is done using a class-specific ensemble feature selection method as follows.

100 bootstrap samples, each comprising the same number of training images, are created by resampling with replacement from the training images. This generates diversities among the bootstrap samples. For each bootstrap sample, the initial collagen features (the initial portal collagen features, initial septa collagen features or initial fibrillar collagen features) are ranked using the support vector machine recursive feature elimination (SVM-RFE) method [39]. In particular, the SVM-RFE method trains a SVM machine using the images in the bootstrap sample and based on this training, extracts the best overall feature subset (i.e. the feature subset that can most accurately separate the images in the bootstrap sample according to the fibrosis stage of the rat liver tissue sample in these images). An ensemble rank of each feature is also generated for each bootstrap sample [43].

The general assumption is that regardless of how the bootstrap sample changes, the important features will tend to remain selected by the SVM-RFE method. Thus, the relevant features to be selected should comprise features which appear the most frequently in the 100 best overall feature subsets extracted for the 100 bootstrap samples. In this example, a cutoff frequency 90% is first set. If a feature is present in at least 90% of the 100 best overall feature subsets extracted, the feature is selected to be one of the relevant collagen features.

Tables 1, 2 and 3 below respectively show the 34 initial portal collagen features, the 28 initial septal collagen features and the 25 initial fibrillar collagen features in this example. As shown in Tables 1-3, these features relate to all the collagen fibers, only the aggregated fibers or only the distributed fibers in each extracted collagen area.

The selected relevant collagen features for one group of training images are highlighted in gray in Tables 1-3. Specifically, 19 relevant portal collagen features for this group of training images are selected as shown in Table 1, 13 relevant septal collagen features are selected as shown in Table 2 and 8 relevant fibrillar collagen features are selected as shown in Table 3.

Figure 12:
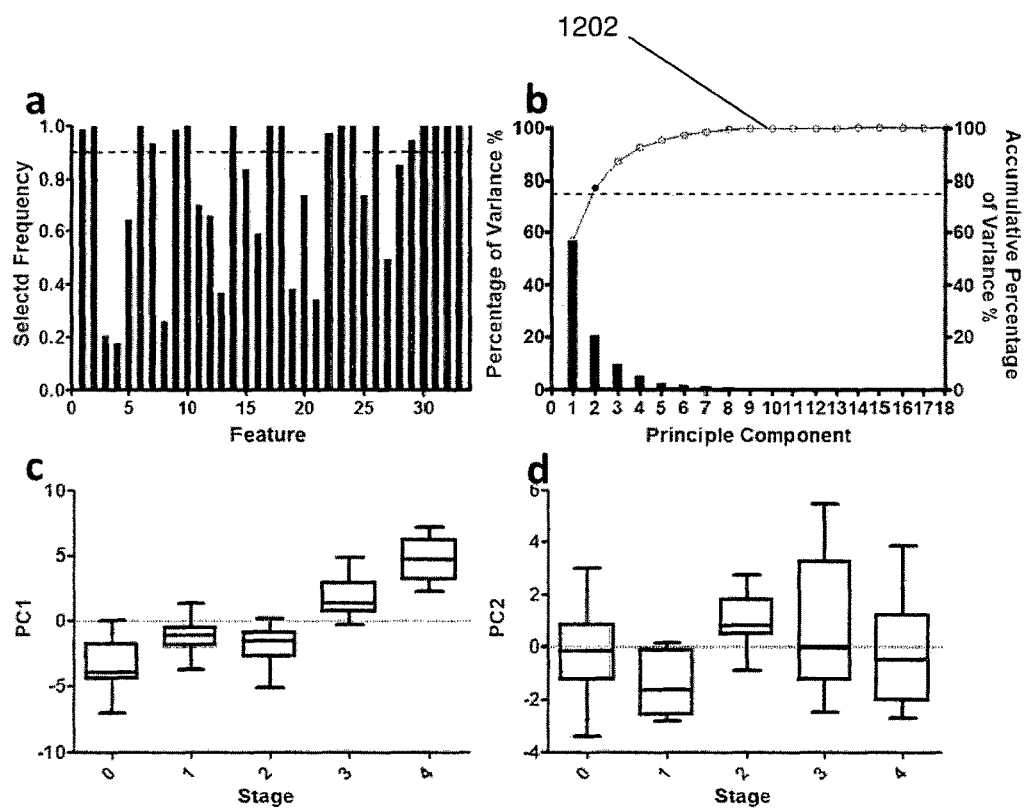
Figure 13:
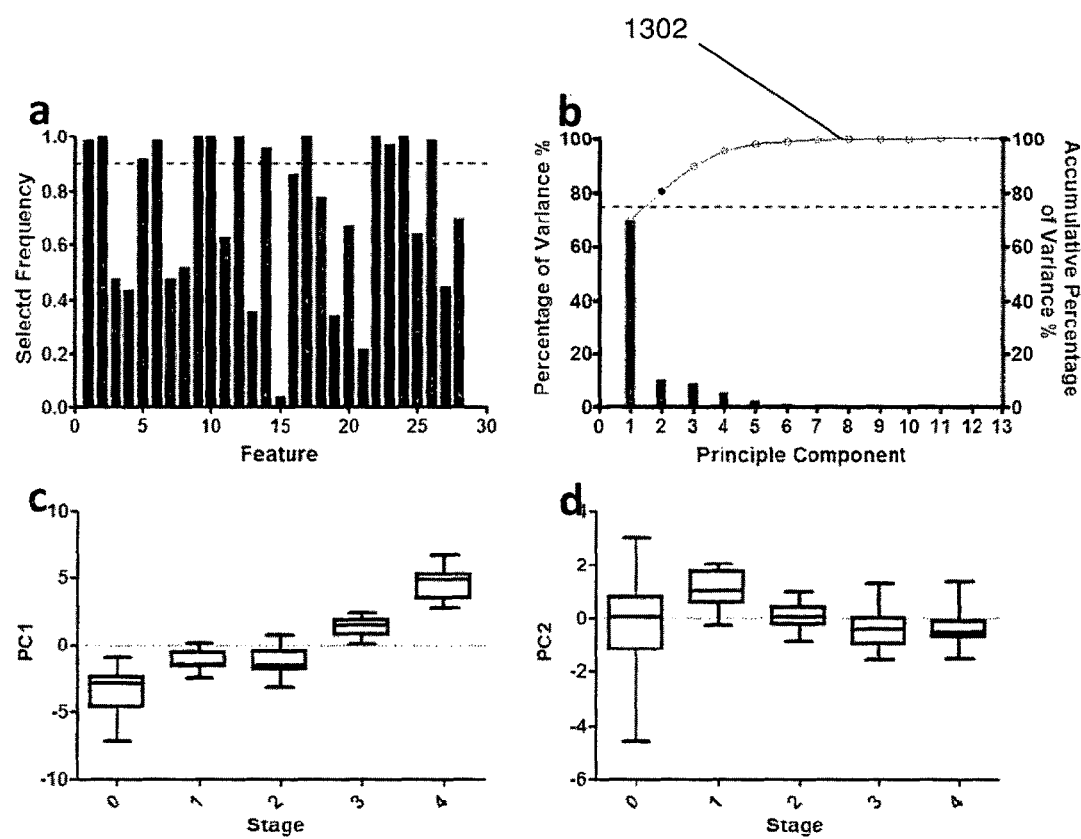
Figure 14:
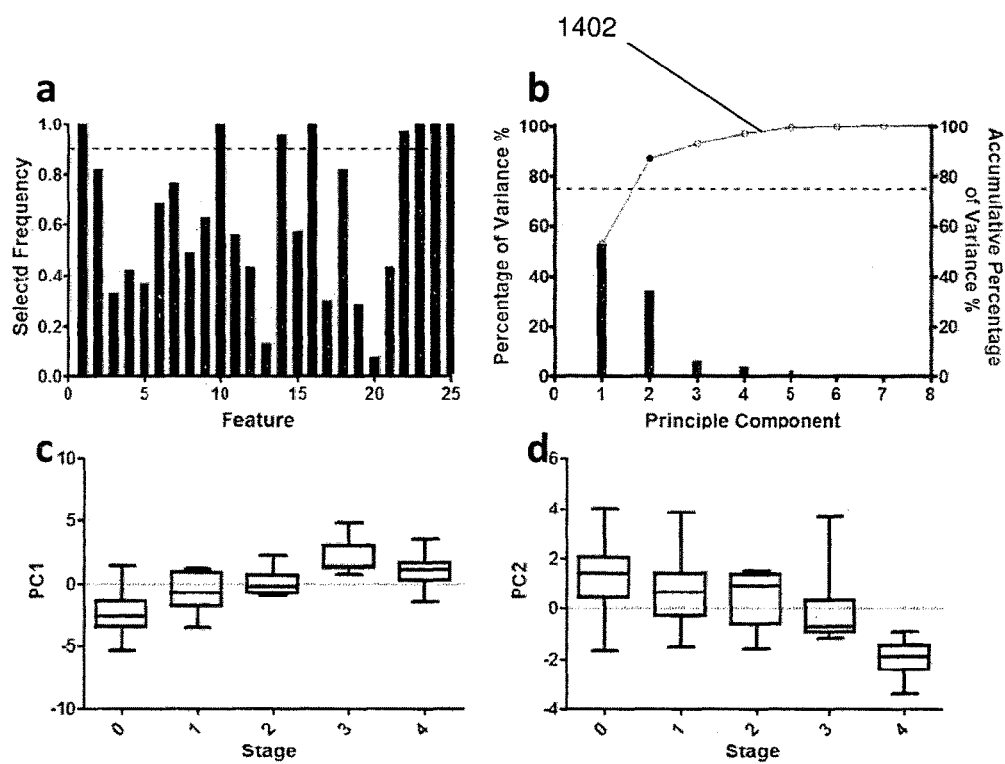

FIGS. 12(a), 13(a), 14(a) respectively show the selection of the 19 relevant portal collagen features from the 34 initial portal collagen features; the selection of the 13 relevant septal collagen features from the 28 initial septal collagen features and the selection of the 8 relevant fibrillar collagen features from the 25 initial fibrillar collagen features.

TABLE 2

| Number | Feature | Description |
|---|---|---|
| 1 | Septal CPA | collagen percentage area calculated as the percentage of pixels representing septal collagen in the extracted septal collagen area |
| 2 | Septal Fiber Number | number of fibers per $mm^2$ in the extracted septal collagen area |
| 3 | Septal Fiber Length | average length of all the fibers in the extracted septal collagen area |
| 4 | Septal Fiber Width | average width of all the fibers in the extracted septal collagen area |
| 5 | Septal Fiber Curvature | average curvature of all the fibers in the extracted septal collagen area |
| 6 | Septal Fiber Alignment | average alignment of all the fibers in the extracted septal collagen area, expressed in terms of a coordination number |
| 7 | Septal Fiber CL Density | average fiber cross-link density of all the fibers in the extracted septal collagen area |
| 8 | Septal Fiber CL Space | average fiber cross-link space of all the fibers in the extracted septal collagen area |

TABLE 1

| Number | Feature | Description |
|---|---|---|
| 1 | Portal CPA | collagen percentage area calculated as the percentage of pixels representing portal collagen in the extracted portal collagen area |
| 2 | Portal Fiber Number | number of fibers per $mm^2$ in the extracted portal collagen area |
| 3 | Portal Fiber Length | average length of all the fibers in the extracted portal collagen area |
| 4 | Portal Fiber Width | average width of all the fibers in the extracted portal collagen area |
| 5 | Portal Fiber Curvature | average curvature of all the fibers in the extracted portal collagen area |
| 6 | Portal Fiber Alignment | average alignment of all the fibers in the extracted portal collagen area, expressed in terms of a coordination number |
| 7 | Portal Fiber CL Density | average fiber cross-link density of all the fibers in the extracted portal collagen area |
| 8 | Portal Fiber CL Space | average fiber cross-link space of all the fibers in the extracted portal collagen area |
| 9 | Portal Agg CPA | percentage of pixels representing aggregated collagen in the extracted portal collagen area |
| 10 | Portal Agg Fiber Number | number of aggregated collagen fibers per $mm^2$ in the extracted portal collagen area |
| 11 | Portal Agg Fiber Length | average length of the aggregated collagen fibers in the extracted portal collagen area |
| 12 | Portal Agg Fiber Width | average width of the aggregated collagen fibers in the extracted portal collagen area |
| 13 | Portal Agg Fiber Curvature | average curvature of the aggregated collagen fibers in the extracted portal collagen area |
| 14 | Portal Agg Fiber Alignment | average alignment of the aggregated fibers in the extracted portal collagen area, expressed in terms of a coordination number |
| 15 | Portal Agg Fiber CL Density | average fiber cross-link density of the aggregated fibers in the extracted portal collagen area |
| 16 | Portal Agg Fiber CL Space | average fiber cross-link space of the aggregated fibers in the extracted portal collagen area |
| 17 | Portal Dis CPA | percentage of pixels representing distributed collagen in the extracted portal collagen area |
| 18 | Portal Dis Fiber Number | number of distributed collagen fibers per $mm^2$ in the extracted portal collagen area |
| 19 | Portal Dis Fiber Length | average length of the distributed collagen fibers in the extracted portal collagen area |
| 20 | Portal Dis Fiber Width | average width of the distributed collagen fibers in the extracted portal collagen area |
| 21 | Portal Dis Fiber Curvature | average curvature of the distributed collagen fibers in the extracted portal collagen area |
| 22 | Portal Dis Fiber Alignment | average alignment of the distributed fibers in the extracted portal collagen area, expressed in terms of a coordination number |
| 23 | Cutoff Width | average of the cut-off distances used for identifying portal collagen pixels in the ROIs in step 704. This "Cutoff Width" represents the average thickness of the portal collagen area i.e. the average thickness of portal collagen around each portal tract region or central vein region in the liver tissue sample, thus reflecting the extent of portal expansion in the liver tissue sample |
| 24 | Portal CPA/ROI | CPA normalized with respect to the number of ROIs (defined in sub-step 602) |
| 25 | Portal Fiber Number/ROI | Portal Fiber Number normalized with respect to the number of ROIs |
| 26 | Portal Agg CPA/ROI | Portal Agg CPA normalized with respect to the number of ROIs |
| 27 | Portal Agg Fiber Number/ROI | Portal Agg Fiber Number normalized with respect to the number of ROIs |
| 28 | Portal Dis CPA/ROI | Portal Dis CPA normalized with respect to the number of ROIs |
| 29 | Portal Dis Fiber Number/ROI | Portal Dis Fiber Number normalized with respect to the number of ROIs |
| 30 | Portal Agg CPA/Portal CPA | ratio of Portal Agg CPA to Portal CPA |
| 31 | Portal Dis CPA/Portal CPA | ratio of Portal Dis CPA to Portal CPA |
| 32 | Portal Agg CPA/Portal CPA/ROI | Portal Agg CPA/Portal CPA normalized with respect to the number of ROIs |
| 33 | Portal Dis CPA/Portal CPA/ROI | Portal Dis CPA/Portal CPA normalized with respect to the number of ROIs |
| 34 | Portal CPA/Total CPA | ratio of Portal CPA to the total percentage of collagen of the liver tissue sample (including portal, septal and fibrillar collagen) |

TABLE 2-continued

| Number | Feature | Description |
|---|---|---|
| 9 | Septal Agg CPA | percentage of pixels representing aggregated collagen in the extracted septal collagen area |
| 10 | Septal Agg Fiber Number | number of aggregated collagen fibers per $mm^2$ in the extracted septal collagen area |
| 11 | Septal Agg Fiber Length | average length of the aggregated collagen fibers in the extracted septal collagen area |
| 12 | Septal Agg Fiber Width | average width of the aggregated collagen fibers in the extracted septal collagen area |
| 13 | Septal Agg Fiber Curvature | average curvature of the aggregated collagen fibers in the extracted septal collagen area |
| 14 | Septal Agg Fiber Alignment | average alignment of the aggregated fibers in the extracted septal collagen area, expressed in terms of a coordination number |
| 15 | Septal Agg Fiber CL Density | average fiber cross-link density of the aggregated fibers in the extracted septal collagen area |
| 16 | Septal Agg Fiber CL Space | average fiber cross-link space of the aggregated fibers in the extracted septal collagen area |
| 17 | Septal Dis CPA | percentage of pixels representing distributed collagen in the extracted septal collagen area |
| 18 | Septal Dis Fiber Number | number of distributed collagen fibers per $mm^2$ in the extracted septal collagen area |
| 19 | Septal Dis Fiber Length | average length of the distributed collagen fibers in the extracted septal collagen area |
| 20 | Septal Dis Fiber Width | average width of the distributed collagen fibers in the extracted septal collagen area |
| 21 | Septal Dis Fiber Curvature | average curvature of the distributed collagen fibers in the extracted septal collagen area |
| 22 | Septal Dis Fiber Alignment | average alignment of the distributed fibers in the extracted septal collagen area, expressed in terms of a coordination number |
| 23 | Septal Agg CPA/ Septal CPA | ratio of Septal Agg CPA to Septal CPA |
| 24 | Septal Dis CPA/ Septal CPA | ratio of Septal Dis CPA to Septal CPA |
| 25 | Septal CPA/ Total CPA | ratio of Septal CPA to the total percentage of collagen of the liver tissue sample (including portal, septal and fibrillar collagen) |
| 26 | Number of Septa/ROI | Number of septa per ROI calculated as the total number of local maxima identified in step 710 normalized by the total number of ROIs |
| 27 | Septa Width | Average septa width or (average thickness of the septal collagen area) calculated as the average width of the local maxima identified in step 710 across all the direction profiles. In this example, the width of a local maximum in a direction profile is expressed in the form of an angle. This is calculated by determining the angles between the local maximum and its neighbouring local maxima, dividing each of the determined angles by two and summing the results of the divisions. For example, for a local maximum M, if the angle between the local maximum M and its first neighbouring local maximum $M_1$ (in the clockwise direction from M) is $\theta_1$ and the angle between the local maximum M and its second neighbouring local maximum $M_2$ (in the counterclockwise direction from M) is $\theta_2$, then the width of the local maximum M is calculated as $\frac{\theta_1}{2} + \frac{\theta_2}{2}$ |
| 28 | Septa Completeness | Average septa completeness between ROIs calculated as the average percentage of collagen along all the local maxima identified in step 710 |

TABLE 3

| Number | Feature | Description |
|---|---|---|
| 1 | Fibrillar CPA | collagen percentage area calculated as the percentage of pixels representing fibrillar collagen in the extracted fibrillar collagen area |
| 2 | Fibrillar Fiber Number | number of fibers per $mm^2$ in the extracted fibrillar collagen area |
| 3 | Fibrillar Fiber Length | average length of all the fibers in the extracted fibrillar collagen area |
| 4 | Fibrillar Fiber Width | average width of all the fibers in the extracted fibrillar collagen area |
| 5 | Fibrillar Fiber Curvature | average curvature of all the fibers in the extracted fibrillar collagen area |
| 6 | Fibrillar Fiber Alignment | average alignment of all the fibers in the extracted fibrillar collagen area, expressed in terms of a coordination number |
| 7 | Fibrillar Fiber CL Density | average fiber cross-link density of all the fibers in the extracted fibrillar collagen area |
| 8 | Fibrillar Fiber CL Space | average fiber cross-link space of all the fibers in the extracted fibrillar collagen area |
| 9 | Fibrillar Agg CPA | percentage of pixels representing aggregated collagen in the extracted fibrillar collagen area |
| 10 | Fibrillar Agg Fiber Number | number of aggregated collagen fibers per $mm^2$ in the extracted fibrillar collagen area |
| 11 | Fibrillar Agg Fiber Length | average length of the aggregated collagen fibers in the extracted fibrillar collagen area |
| 12 | Fibrillar Agg Fiber Width | average width of the aggregated collagen fibers in the extracted fibrillar collagen area |
| 13 | Fibrillar Agg Fiber Curvature | average curvature of the aggregated collagen fibers in the extracted fibrillar collagen area |
| 14 | Fibrillar Agg Fiber Alignment | average alignment of the aggregated fibers in the extracted fibrillar collagen area, expressed in terms of a coordination number |
| 15 | Fibrillar Agg Fiber CL Density | average fiber cross-link density of the aggregated fibers in the extracted fibrillar collagen area |
| 16 | Fibrillar Agg Fiber CL Space | average fiber cross-link space of the aggregated fibers in the extracted fibrillar collagen area |
| 17 | Fibrillar Dis CPA | percentage of pixels representing distributed collagen in the extracted fibrillar collagen area |
| 18 | Fibrillar Dis Fiber Number | number of distributed collagen fibers per $mm^2$ in the extracted fibrillar collagen area |
| 19 | Fibrillar Dis Fiber Length | average length of the distributed collagen fibers in the extracted fibrillar collagen area |
| 20 | Fibrillar Dis Fiber Width | average width of the distributed collagen fibers in the extracted fibrillar collagen area |
| 21 | Fibrillar Dis Fiber Curvature | average curvature of the distributed collagen fibers in the extracted fibrillar collagen area |
| 22 | Fibrillar Dis Fiber Alignment | average alignment of the distributed fibers in the extracted fibrillar collagen area, expressed in terms of a coordination number |

TABLE 3-continued

| Number | Feature | Description |
|---|---|---|
| 23 | Fibrillar Agg CPA/Fibrillar CPA | ratio of Fibrillar Agg CPA to Fibrillar CPA |
| 24 | Fibrillar Dis CPA/Fibrillar CPA | ratio of Fibrillar Dis CPA to Fibrillar CPA |
| 25 | Fibrillar CPA/Total CPA | ratio of Fibrillar CPA to the total percentage of collagen of the liver tissue sample (including portal, septal and fibrillar collagen) |

Step 106

In this example, for each test image and its corresponding group of training images, only quantitative values of the relevant features selected during step 206 (using the corresponding group of training images) are obtained for the test image in step 106. For instance, for the group of training images associated with the relevant features highlighted in gray in Tables 1-3, only the quantitative values of these features are obtained for the corresponding test image in step 106 of method 100.

The quantitative values of the features are obtained in step 106 in the same manner as described above for step 206.

Step 208 and Step 108

In this example, steps 108 and 208 are implemented by performing the following steps on the quantitative values of each set of relevant collagen features (i.e. the relevant portal collagen features, the relevant septal collagen features or the relevant fibrillar collagen features) in each image (either the test image or a training image).

PCA is first performed on the quantitative values of the set of relevant collagen features to obtain un-correlated principal components (PCs). Each PC obtained from the PCA is a weighted summation of the features (each feature having a different weight), with the first principal component having the largest possible variance (i.e. it represents most of the variability in the features) and each subsequent PC having a lower possible variance than its previous PC.

Then, PCs satisfying the following component selection criteria are selected: (1) the accumulative percentage of variance of all the selected PC should exceed 75% of the total variance of the features and (2) each selected PC should have a variance no less than 10% of the total variance of the features.

The selected PCs are then output from step 108 or step 208. In other words, three sets of PCs (portal PCs, septal PCs and fibrillar PCs respectively obtained from the relevant portal collagen features, the relevant septal collagen features and the relevant fibrillar collagen features) are output for each image, with each set of PCs comprising the respective selected PCs.

FIGS. 12(b), 13(b), 14(b) respectively show the PCs obtained after performing the PCA on the relevant portal collagen features from Table 1, the relevant septal collagen features from Table 2 and the relevant fibrillar collagen features from Table 3 of an acquired image in this example. FIGS. 12(b), 13(b), 14(b) each further shows a graph 1202, 1302, 1402 plotting the accumulative percentage of variance represented by the PCs.

In particular, it can be seen from FIGS. 12(b), 13(b), 14(b) that the two most significant PCs [39] account for a large part (more than 75% in FIG. 12(b), close to 80% in FIG. 13(b) and more than 80% in FIG. 14(b)) of the total variance of the respective selected relevant collagen features, whereas each of these two most significant PCs also accounts for more than 10% of this total variance. Therefore, based on the component selection criteria as mentioned above, the first and second significant PCs are selected for all the sets of relevant collagen features.

FIGS. 12(c) and (d) respectively show the values of the first and second significant PCs obtained for the relevant portal collagen features in all the acquired images in this example, FIGS. 13(c) and (d) respectively show the values of the first and second significant PCs obtained for the relevant septal collagen features in all the acquired images in this example, and FIGS. 14(c) and (d) respectively show the values of the first and second significant PCs obtained for the relevant fibrillar collagen features in all the acquired images in this example. In each of FIGS. 12(c)-(d), 13(c)-(d), 14(c)-(d), the values are plotted against the fibrosis stages associated with the images from which the values are obtained.

As shown in FIGS. 12(c), 13(c), 14(c), there is generally an increasing trend in the value of the first PC as fibrosis progresses to later stages for all the sets of relevant collagen features. This is probably because majority of the selected relevant features change as fibrosis progresses. On the other hand, FIGS. 12(d), 13(d), 14(d) show that the second PC was only sensitive to differences between fibrosis stages 1 and 2. This sensitivity of the second PC is probably due to changes in the distributed collagen percentage (i.e. Dis CPA) and the distributed collagen fiber number (i.e. Dis Fiber Number) as fibrosis progresses from stage 1 to 2. Thus, it can be seen from FIGS. 12(c), 13(c), 14(c) that by selecting PCs based on the component selection criteria mentioned above in this example, accurate and efficient assessment of liver fibrosis can be performed as changes in the morphological features during fibrosis progression can be reflected by the selected PCs.

Step 210

In this example, for each group of training images, a first, second, third and fourth multinomial logistic regression model is respectively trained using all the PCs, the portal PCs, the septal PCs and the fibrillar PCs obtained in step 208 to provide an overall set of parameters, a portal set of parameters, a septal set of parameters and a fibrillar set of parameters.

These overall set of parameters, portal set of parameters, septal set of parameters and fibrillar set of parameters are collectively output from step 210 as the set of parameters representing the trained model.

Step 110

In this example, statistics reflecting the degree of fibrosis in each test liver tissue sample are generated based on the PCs obtained in step 108 for the test liver tissue sample and its corresponding trained model obtained in step 210 as mentioned above. These statistics include probabilities that the liver tissue sample is at a particular fibrosis stage, a portal index, a septal index, a fibrillar index and a qFibrosis index.

Figure 15:
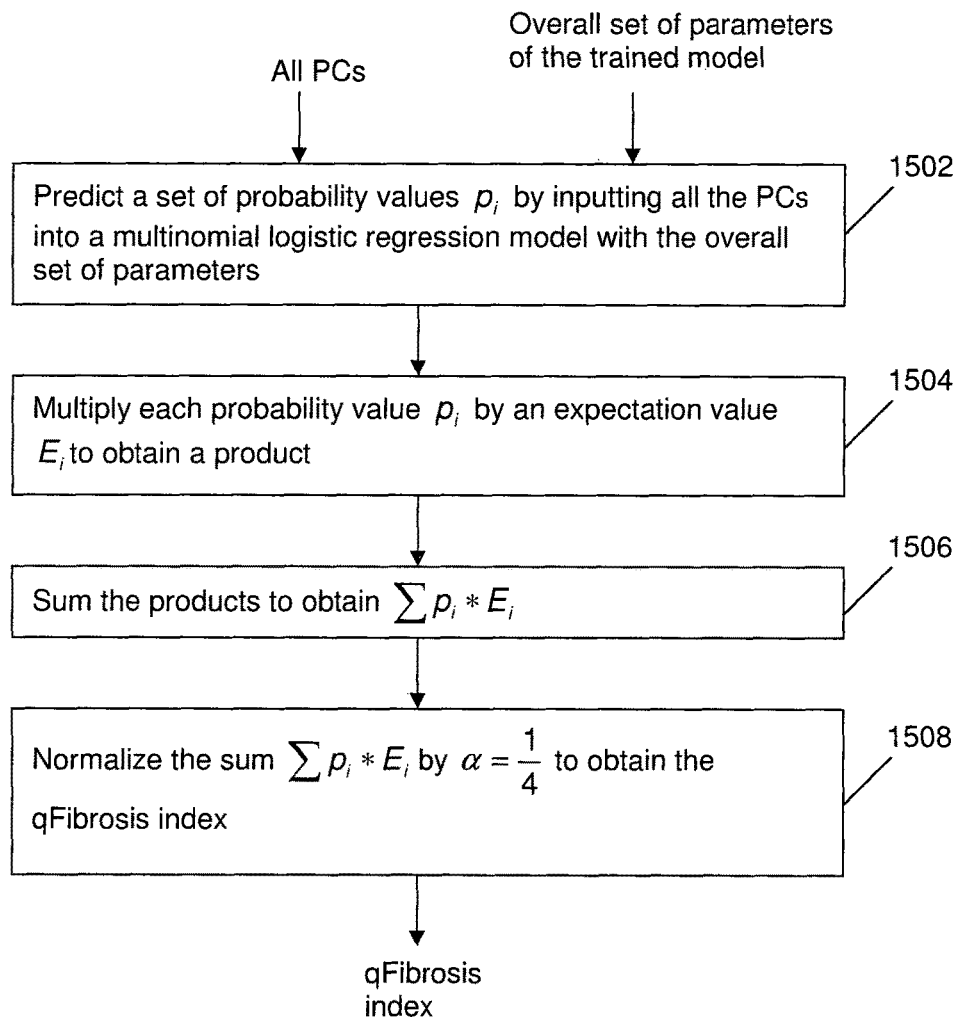
FIG. 15 shows a flow diagram of steps used to obtain a qFibrosis index in the example implementation of FIG. 3.

FIG. 15 shows the steps 1502-1508 to obtain the qFibrosis index in this example. In particular, in step 1502, a set of probability values $p_i$ is first predicted by inputting all the PCs into a multinomial logistic regression model using the overall set of parameters. Each probability value $p_i$ indicates the probability that the test liver tissue sample is at a particular fibrosis stage i. A qFibrosis index is then obtained using Equation (1) above and the probability values $p_i$ from sub-step 1502. More specifically, in step 1504, each probability value $p_i$ is first multiplied by an expectation value $E_i$ (which is set as i) to obtain a product. In step 1506, the products obtained in step 1504 are then summed to obtain $\Sigma p_i * E_i$ and subsequently, in step 1508, this sum $\Sigma p_i * E_1$ is normalized by $$\alpha = \frac{1}{4}$$

to produce the qFibrosis index. The resulting qFibrosis index is a continuous variant located in the range 0 to 1.

The portal index, septal index and fibrillar index are obtained in a manner similar to that described above for qFibrosis index. However, to obtain the portal index, in step 1502, only the portal PCs are inputted and the multinomial logistic regression model uses the portal set of parameters instead of the overall set of parameters. To obtain the septal index, in step 1502, only the septal PCs are inputted and the multinomial logistic regression model uses the septal set of parameters. To obtain the fibrillar index, in step 1502, only the fibrillar PCs are inputted and the multinomial logistic regression model uses the fibrillar set of parameters.

Figure 16:
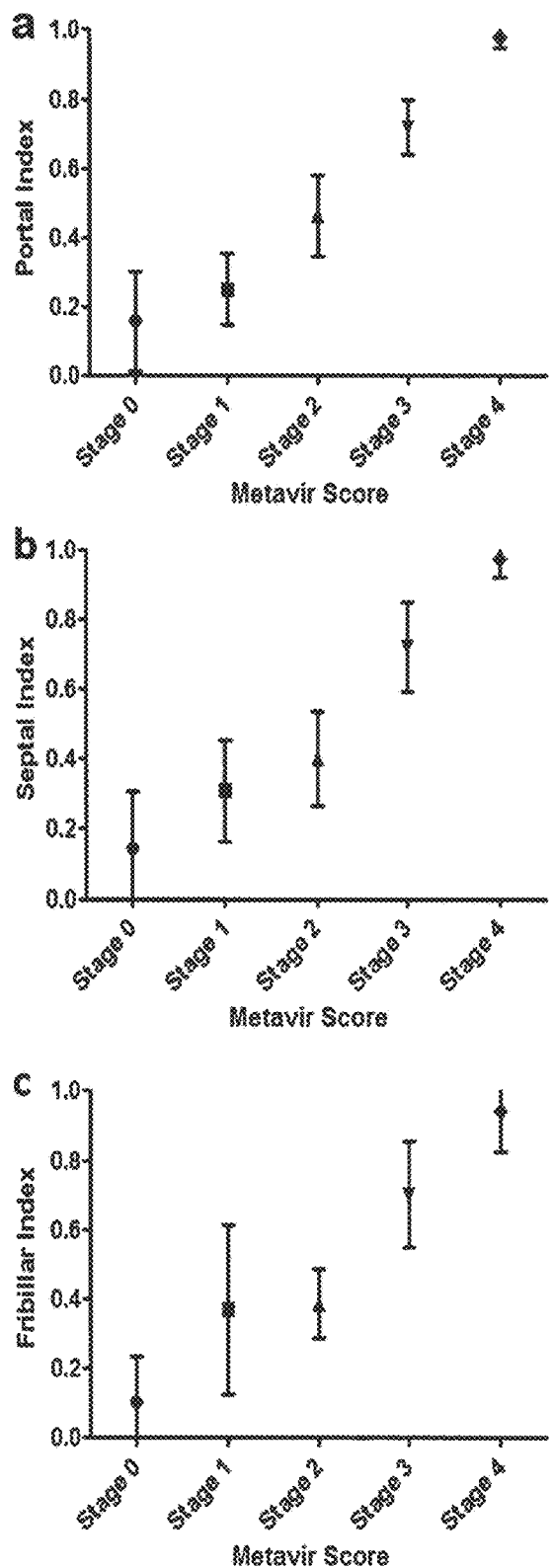
FIGS. 16(a)-(c) respectively show results associated with portal indices, septal indices and fibrillar indices obtained in the example implementation of FIG. 3.

FIGS. 16(*a*)-(*c*) respectively show the portal indices, septal indices and fibrillar indices obtained for all the acquired images in this example. These indices are plotted against the fibrosis stages (Metavir scores) associated with the images from which the indices are obtained. As shown in FIGS. 16(*a*)-(*c*), the portal index changes the most between fibrosis stages 1 and 2 whereas the septal index changes the most between fibrosis stages 2 and 3. This is consistent with the histo-pathological knowledge that portal expansion occurs before septal collagen formation and extension in the progression of fibrosis.

Alternatives to the Example Implementation of Method 100

Many variations to the above example implementation of method 100 are possible within the scope of the invention, as defined by the claims. A few examples of such variations are given below.

For example, method 100 may be implemented in the same manner on human biopsy liver tissue samples or other types of animal liver tissue samples. With according changes to method 100 which will be apparent to one skilled in the art, method 100 can also be used to assess fibrosis in tissues other than the liver. For example, the above example implementation can be adapted to assess fibrosis in organ systems such as chronic glomerulopathies.

Also, instead of using the intensity values of the pixels for identifying collagen areas and lumen areas in steps 102 and 202, color values, texture values or any other values associated with the pixels can be used. The type of values to be used may be selected based on the contrast agent used in the imaging procedures.

Furthermore, in step 704, the cut-off distance may be calculated in a different manner. For example, the cut-off distance may be set as the distance at which the collagen percentage decreases to a different proportion of the maximum collagen percentage. This different proportion may be a percentage between 40% to 60%. In addition, in step 708, the direction profile may comprise direction percentages for any number of directions. The number of directions and the separation between the directions (which need not be constant) may be tuned using a plurality of ROIs with manually identified septal collagen as references. The predetermined percentage threshold used in step 710 may also be tuned in the same manner.

Other threshold values used in the example implementation of method 100 may also be varied. These include for instance, the thresholds for defining small areas and areas having irregular shapes when identifying lumens from the TPEF image in step 102 or 202, the threshold for determining the local minimum directions in step 1110 and the threshold for determining whether the pixels orientation of a major axis is close to the orientation of a local minimum direction in step 1110.

Furthermore, although sub-steps 902-906 are performed simultaneously using parallel computing in the above example, they may alternatively be performed sequentially.

Moreover, the removal of pixels in step 1104 to extract the skeleton of each collagen segment may be performed using means other than morphological erosion, provided that the constraint (that for all the collagen segments, before the stopping condition is valid, removal of the boundary pixels of the most recently generated skeleton will not result in a structure having two or more disconnected groups of pixels) remains satisfied.

Furthermore, in steps 108 and 208, the quantitative values may be converted using other transformation techniques such as the partial least squares (PLS) technique.

The trained model also need not use the multinomial logistic regression model even though, such a model is preferable as it can produce multiple e.g. five or seven outcomes (or more specifically, probabilities) for each test image.

In addition, although the above implementation of method 100 uses the Metavir scoring system, it may be modified to use the Ishak scoring system instead.

System for Implementing Methods 100 and 200

Figure 17:
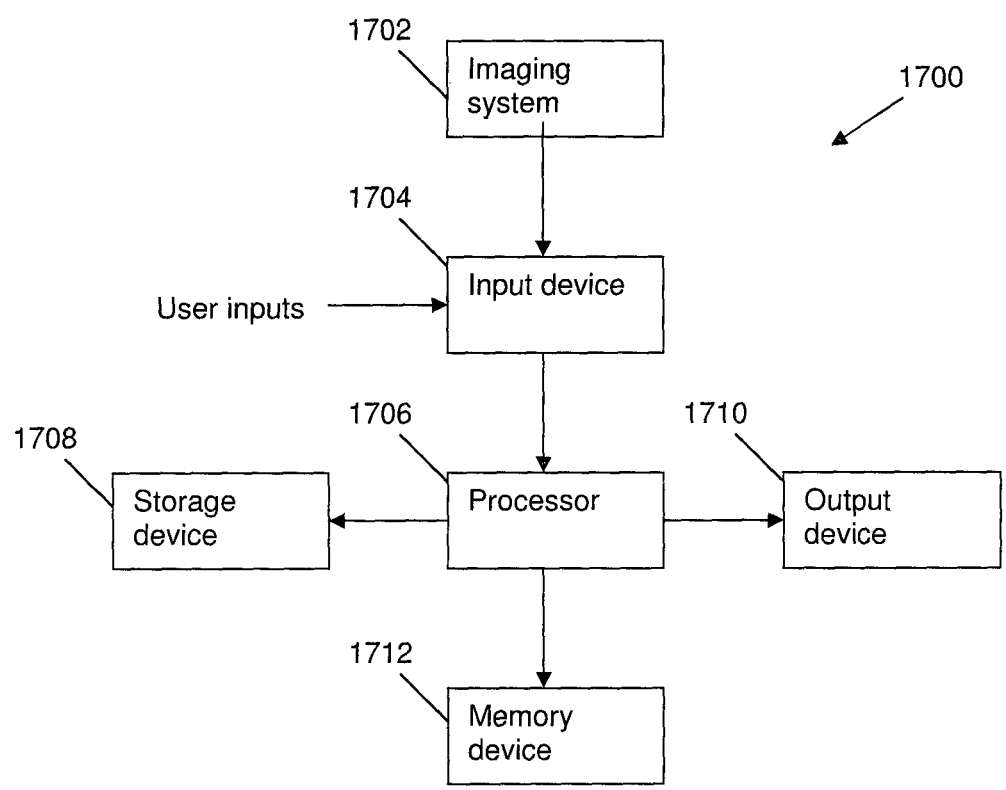
FIG. 17 shows a system for implementing the methods of FIGS. 1 and 2 according to an embodiment of the present invention.

FIG. 17 shows a system 1700 for implementing methods 100 and 200 according to an embodiment of the present invention.

In particular, the system 1700 comprises an imaging system 1702 for acquiring the test and training images. This imaging system 1702 may be a microscope or a whole slide scanner.

The system 1700 also comprises an input device 1704 for receiving the inputs to methods 100 and 200 (including the images from the imaging system 1702 and user inputs from a human operator). The user inputs from the human operator may include instructions such as whether the acquired images are for training the model or for input to method 100, or ground truths associated with the training images.

The system 1700 further comprises a computing platform or data processing platform which in turn comprises a processor 1706, a storage device 1708, an output device 1710 and a memory device 1712. The processor 1706 is configured to perform methods 100 and 200, and can be local (e.g. a local computer) or remote (e.g. a remote server). The memory device 1712 is configured to temporarily store the acquired images and any data required during the implementation of methods 100 and 200. The storage device 1708 can also be local or remote, and is configured to store the parameters representing the trained model. The statistics generated from method 100, and the quantitative values calculated for the acquired images can also be stored in the storage device 1708. The statistics generated from method 100 can also be further transferred to the output device 1710 for display.

Applications of Method 100

Method 100 can be used for many applications. For example, method 100 can be used for the precise analysis of liver fibrosis in both basic research and medical practice, as demonstrated in the example implementation described above. Method 100 is also a great complementary tool for conventional semi-quantitative histopathology liver fibrosis assessment methods and for the current gold standard practice of liver biopsy fibrosis assessment. For instance, pathologists often face difficulties deciding the fibrosis stages of test biopsy tissue samples which are of a bad quality, such as small biopsy tissue samples shorter than 15 mm. In this case, by using a model trained with biopsy tissue samples of a good quality (i.e. samples longer than 15 mm), method 100 serves as a good complementary tool to assist pathologists in deciding and adjusting their fibrosis stages of the test biopsy tissue samples of a bad quality. Furthermore, method 100 can be used as an educational tool to train inexperienced pathologists. In particular, a model can first be trained using knowledge from an experienced pathologist (e.g. with the experienced pathologist deciding the fibrosis stage of the tissue in each training image) and then be used in method 100 to obtain results for a series of test images. These results can be employed to assist inexperienced pathologists in deciding the fibrosis stages of the tissues in the test images and thus, can help in educating the inexperienced pathologists.

Furthermore, method 100 is a powerful tool for evaluating incremental treatment efficacies. Such evaluation is useful for anti-fibrotic drug development and related research of chronic liver diseases. Besides liver fibrosis, method 100 can also be used for applications in the field of oncology, namely, in the assessment of tumour desmoplasia and the response to treatments in this field (which may be indicated by for example, the amount of post-treatment scarring).

Specifically, the statistics generated in method 100 can be used in many applications. Three examples of such applications are diagnosis of the patient from which the test image is obtained from, evaluation of treatment efficacy on the patient, and validation of other diagnosis tools. For example, the fibrosis stage of a patient's liver may be estimated based on the probabilities generated in the example implementation. Moreover, in the example implementation, as the generated indices are sensitive to small changes in the patient's liver, test images from a patient undergoing a particular treatment can be acquired over a period of time and the indices can be generated for each test image to evaluate the efficacy of the treatment. Furthermore, the indices generated for the test images acquired over the period of time can be compared against measurements generated for these test images by newly-developed tools to validate the performance of these newly-developed tools. The indices can also serve as surrogate histological markers and are usable in any application where histo-pathological evaluation is needed.

Advantages of Method 100

The following describes some advantages of method 100.

Method 100 does not Require Staining of Tissue Samples

Method 100 can be used with images that are obtained with stain-free imaging technology (i.e. imaging technology that does not require staining of the samples). For example, method 100 can use images obtained with SHG microscopy [14-16] and TPEF microscopy. This is illustrated in the example implementation of method 100 above.

The absence of the need for staining of tissue samples allows the complete avoidance of staining artefacts which in turn helps to achieve simultaneous accurate assessment of for example, collagen content and morphological information of the tissue samples [17]. The absence of the need for staining and digestion of tissue samples also makes it easier to use method 100 in various studies without interrupting existing protocols, or requiring extra information or material. Furthermore, using the SHG technique in method 100 is particularly advantageous as the SHG technique can provide 3D visualization capability of thick tissue samples without the need to stain these tissue samples [18], thus allowing for real-time 3D examination of tissue samples down to the cellular level.

Method 100 is Fully Automatic

Furthermore, method 100 is fully automatic. By "automatic", it is meant that although human interaction may initiate the algorithm, human interaction is not required while the algorithm is carried out (although, method 100 may alternatively be performed semi-automatically, in which case there is human interaction with the computer during the processing).

Method 100 is Fully Quantitative

Another advantage of method 100 is that it is fully quantitative and hardly relies on user observations which are usually highly subjective due to inter- and intra-observer discrepancies.

The Example Implementation of Method 100 Uses Quantitative Values of Features from Three Different Types of Collagen Areas Method 100, in particular, the example implementation is advantageous as it uses quantitative values of features from three different types of collagen areas (the portal collagen area, the septal collagen area and the fibrillar collagen area) to assess liver fibrosis. This is in contrast to many of the current staging/scoring systems for chronic viral infection and chronic cholestatic disorders whereby changes in fibrillar collagen, i.e. collagen in the pericellular/perisinusoidal space, are not addressed in detail [23-25]. Moreover, since the portal collagen, septal collagen and fibrillar collagen areas are pathologically relevant, using quantitative values of features from these three different types of collagen areas is advantageous over using features from other areas which are not pathologically relevant.

Note that although the method in a previous application PCT/SG2011/000133 by the inventors also identifies two different types of collagen areas, namely normal and abnormal collagen areas, and calculates the CPA for each of these two types of collagen areas, this method is different from method 100 as it does not identify the portal collagen, septal collagen and fibrillar collagen areas.

Because of the use of quantitative values of features from the three different types of collagen areas, the statistics generated in the example implementation can be used to accurately track morphological changes in a patient's liver by obtaining images of the patient's liver over time. Specifically, the amount of portal expansion in the patient's liver can be tracked using the portal index, the amount of fibrosis bridging in the patient's liver can be tracked using the septal index, and the general distribution of fine collagen throughout the patient's liver can be tracked using the fibrillar index. These changes have been observed during the dynamic process of fibrosis progression [20] and thus, by tracking these changes, the state of fibrosis in the patient's liver over time can be determined.

The qFibrosis index is generated from features obtained from all three types of collagen structures and thus, in some sense, is a combination of the other three indices: portal index, septal index and fibrillar index. While it is commonly expected that these three indices would increase as fibrosis progresses, it was found that the effectiveness of each index in detecting different stages of fibrosis progression is different (for example, an index may be more sensitive in detecting stage 2 fibrosis). Thus, the qFibrosis index being a combination of all three indices can detect finer incremental fibrosis changes in the liver over time and can be used to investigate regression patterns in cirrhosis. Therefore, the qFibrosis index is very useful in prognostic applications.

The ability of method 100 to generate statistics based on the three types of collagen structures is in turn due to the ability of the algorithms used in method 100 to differentiate the various types of collagen accurately and automatically.

For example, from FIG. 8, it can be seen that different types of collagen areas can be successfully distinguished using method 100 regardless of the stage of fibrosis in the tissue sample.

The Example Implementation of Method 100 Uses Quantitative Values of Features from Aggregated Collagen Fibers and Distributed Collagen Fibers In the example implementation, method 100 separates the fibers in each type of collagen area into aggregated and distributed collagen fibers, and uses quantitative values of features from each of these two types of fibers. This also helps to track morphological changes in the patient's livers.

For example, the use of features such as "Agg CPA/CPA" and "Dis CPA/CPA" which are able to reflect the dynamic changes in aggregated and distributed portal collagen as fibrosis progresses can help to track morphological changes associated with these dynamic changes.

The Example Implementation of Method 100 Uses Features which are Robust to the Part of the Tissue Imaged FIG. 18 shows a quantitative comparison between some of the features used in the example implementation of method 100 and the CPA measurement. The comparison in FIG. 18 is performed using images of three different sections 1802, 1804, 1806 of a rat liver tissue sample at a late stage fibrosis (F4) acquired in the example implementation of method 100 as described above.

As shown in FIG. 18, the CPA measurement obtained for the different sections 1802-1806 varied significantly from 11.47% to 20.79%, indicating the sensitivity of the CPA method to the part of the tissue sample that is imaged. Similar findings about this sensitivity of the CPA have been reported in the prior art. In fact, Standish et al. [21] in their summary have stated that CPA and histopathology scoring are entirely different assessment methods of liver fibrosis.

On the other hand, as shown in FIG. 18, the percentages of portal CPA (Portal CPA/CPA), percentages of septal CPA (Septa CPA/CPA) and percentages of fibrillar CPA (Fibrillar CPA/CPA) obtained for the three sections 1802-1806 varied much less. Specifically, the coefficients of variation, defined as standard deviation divided by the mean, of these percentages are much smaller than that of the CPA measurement. In other words, as compared to the CPA measurement, these percentages (Portal CPA/CPA, Septa CPA/CPA, Fibrillar CPA/CPA) are much less sensitive to the part of the tissue sample that is imaged. The same applies for architectural measurements, such as the portal collagen thickness (i.e. "Cutoff Width") and the septal collagen thickness (i.e. "Septal Width"). This demonstrates the advantages of characterizing collagen architectural changes over just using the CPA measurement in the assessment of liver fibrosis.

The Example Implementation of Method 100 can Still Perform Well Even with Small Tissue Samples Inadequate biopsy size has been cited as one of the main factors that can impact the accuracy of fibrosis assessment in most clinical practices [26]. It has been recommended that the minimum length of a tissue sample should be 20 mm for assessing chronic viral hepatitis [27]. However, the systematic review by Standish et al. showed that in practice the average biopsy length of tissue samples is only 13.5 mm [21]. Therefore, it is desirable to have a method that works well regardless of the size of the biopsy sample available.

As compared to the CPA method, the example implementation of method 100 is more robust to the size of the test tissue sample and can perform better with small tissue samples as it uses morphological features that are less sensitive (as compared to the CPA measurement) to the size of the tissue sample.

In particular, Table 4 shows a comparison between the CPA measurement and the qFibrosis index for differently-sized images. These differently-sized images are obtained from the rat liver tissue samples acquired in the example implementation described above by cropping the acquired images of these samples into half, one fourth, one eighth and one sixteenth of the original sizes. The resulting sizes of the images ranged from 1 $mm^2$ to 16 $mm^2$.

TABLE 4

| Stage | Sample Size | | | | |
|---|---|---|---|---|---|
| | 16 $mm^2$ | 8 $mm^2$ | 4 $mm^2$ | 2 $mm^2$ | 1 $mm^2$ |
| | CPA | | | | |
| 0 vs. 1 | 0.819 | 0.774 | 0.716 | 0.681 | 0.637 |
| 1 vs. 2 | 0.668 | 0.647 | 0.636 | 0.612 | 0.563 |
| 2 vs. 3 | 0.924 | 0.851 | 0.820 | 0.778 | 0.738 |
| 3 vs. 4 | 0.876 | 0.844 | 0.794 | 0.773 | 0.743 |
| | qFibrosis | | | | |
| 0 vs. 1 | 0.876 | 0.915 | 0.840 | 0.805 | 0.744 |
| 1 vs. 2 | 0.806 | 0.736 | 0.778 | 0.734 | 0.742 |
| 2 vs. 3 | 0.990 | 0.941 | 0.952 | 0.902 | 0.841 |
| 3 vs. 4 | 0.929 | 0.890 | 0.866 | 0.886 | 0.856 |

Specifically, Table 4 shows the AUC values of the CPA measurement and the qFibrosis index obtained for the differently-sized images. As shown in Table 4, the AUC values of both CPA measurement and qFibrosis index were found to decrease as the size of the input images decreases. However, it can be seen that regardless of the size of the input images, the qFibrosis index performs better than CPA measurement in differentiating liver tissue samples at different stages of fibrosis. In fact, the performance of the qFibrosis index when the input images are 1 $mm^2$ in size were found to be similar to that of the CPA measurement when the input images are 8 $mm^2$ in size. Even at the smallest image size tested (i.e. 1 $mm^2$), the AUC obtained for the qFibrosis index can reach around 0.75 for early fibrosis detection and above 0.85 for late fibrosis detection. On the other hand, the CPA failed to perform well for early fibrosis detection (in particular, its AUC is less than 0.65) with the smallest image size. Furthermore, the AUCs obtained for method 100 vary less across the different images as compared to those obtained for the CPA method.

The Example Implementation of Method 100 Correlates Better with Histopathology Scores than the CPA Method The two tailed Wilcoxon rank-sum test was used to estimate the significance in the statistical differences of CPA measurements and of qFibrosis indices across liver tissue samples at different Metavir stages. The Wilcoxon rank-sum test, together with the ROC analysis, was performed at a significance level of 0.05 using Matlab software (The Math Works, Natick, Mass.) and its statistical toolbox.

Figure 19:
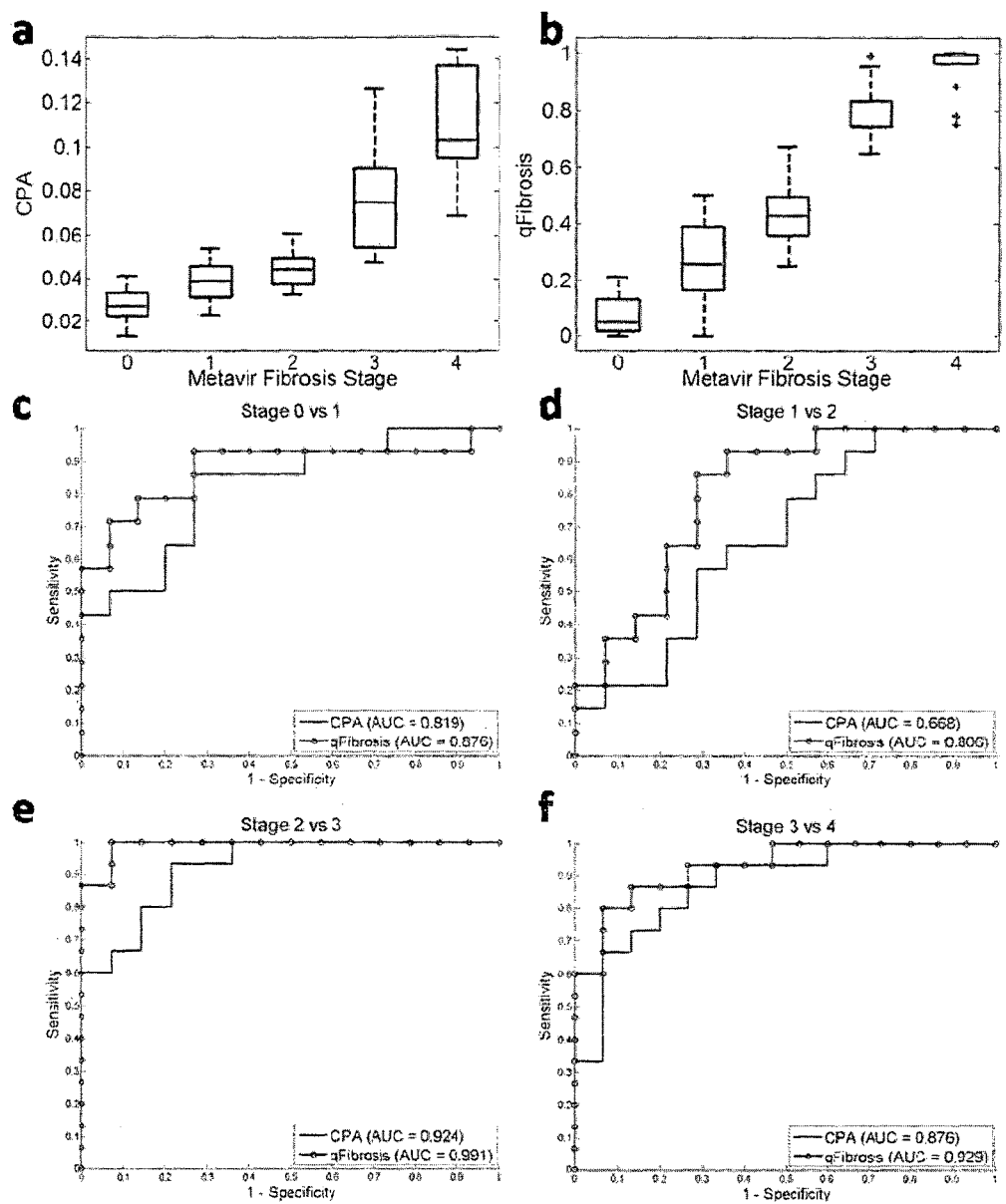
FIGS. 19(a)-(b) show the distribution of CPA measurements and qFibrosis indices obtained in the example implementation of FIG. 3 across different fibrosis stages.
FIGS. 19(c)-(f) show receiver operating curves (ROCs) of the CPA measurements and the qFibrosis indices obtained in the example implementation of FIG. 3.

FIGS. 19(a)-(b) are box plots showing the distribution of qFibrosis indices and CPA measurements across different fibrosis stages whereas FIGS. 19(c)-(f) show receiver operating curves (ROCS) of the CPA measurements and qFibrosis indices indicating how well the CPA measurement and qFibrosis index differentiates between liver tissue samples at different fibrosis stages.

In particular, FIG. 19(a) and FIG. 19(b) respectively shows the CPA measurements and qFibrosis indices of liver tissue samples at different fibrosis stages. As shown in FIG. 19(a), the CPA measurement was found to increase exponentially with the progression of fibrosis across the different stages. This is consistent with previous reports [10-13, 20]. Although the CPA measurement was shown to exhibit a dramatic increase for liver tissue samples at late fibrosis stages, the difference between the CPA measurements of liver tissue samples at early stages and those at mid-stages were not significant (stage 1 versus stage 2: p=0.106). On the other hand, the qFibrosis index showed a more linear increasing trend. Moreover, significant differences ($p<0.001$) were present in the qFibrosis indices of the liver tissue samples across all fibrosis stages.

FIGS. 19(c)-(f) show receiver operating characteristic (ROC) curves of the CPA measurement and qFibrosis index in differentiating between liver tissue samples at fibrosis stages 0 and 1, differentiating between liver tissue samples at fibrosis stages 1 and 2, differentiating between liver tissue samples at fibrosis stages 2 and 3 and differentiating between liver tissue samples at fibrosis stages 3 and 4 respectively. The superiority of the qFibrosis index over the CPA measurement to distinguish between liver tissue samples at all fibrosis stages can be seen from FIGS. 19(c)-(f). Specifically, for the diagnosis of early fibrosis in liver tissue samples (i.e. for distinguishing between liver tissue samples at fibrosis stages 0 and 1), the area under curve (AUC) for the qFibrosis index was found to be 0.88 whereas that for the CPA measurement was found to be only 0.82. Furthermore, while it is difficult to differentiate between liver tissue samples at stages 1 and 2 using the CPA measurement, the qFibrosis index is able to achieve this differentiation with an AUC of around 0.8. For the diagnosis of liver tissue samples at later fibrosis stages, while both CPA measurement and the qFibrosis index worked well, higher AUC values were still provided by the qFibrosis index as compared to the CPA measurement when differentiating between liver tissue samples at fibrosis stages 2 and 3, and when differentiating between liver tissue samples at fibrosis stages 3 and 4. Thus, from FIGS. 19(c)-(f), it can be seen that the qFibrosis index is more sensitive and specific than the CPA.

Method 100 is Useful in Determining Treatment Plans for Fibrosis

The qFibrosis index can serve as a fibrosis risk score and can be incorporated into a decision-making framework for determining how urgently antifibrotic therapy is needed. For example, as mentioned above, the qFibrosis index can assist pathologists in determining the fibrosis stages of tissues. With paired biopsy tissue samples from a patient, the qFibrosis index can also help in monitoring and predicting the progression rate of fibrosis in the patient's tissue. Thus, the qFibrosis index can help in obtaining information important for the decision of treatment plans.

Currently, the only curative treatment for end stage cirrhosis is transplantation and no drug has yet been approved as an antifibrotic. A description of the current clinical trials for the development of antifibrotic drugs can be found in reference [44]. A major difficulty in developing antifibrotic therapies is the lack of accurate and established techniques to estimate fibrosis regression in response to the therapies. This difficulty can at least be partially overcome using method 100 as after administering treatment to a patient, the qFibrosis index or indices obtained using one or more biopsy tissue samples from the patient can be used to monitor fibrosis regression. This allows the evaluation of the treatment efficacy and in turn, facilitates the decision on whether modification of the treatment plans is required.

Thus, a method of treating a patient having fibrosis may comprise administering antifibrotic therapy based on an assessment of fibrosis in a tissue of the patient, whereby the assessment (which may be in the form of the qFibrosis index) is obtained using method 100. The antifibrotic therapy may involve the use of antifibrotic drugs or other therapies, for instance, those described in reference [44], the contents of which are hereby incorporated by reference. Specifically, the antifibrotic therapy may aim to achieve one or more of the following: (i) eliminate the cause(s) of injury and their mediators; (ii) reduce inflammation and the immune response; (iii) target specific signaling: receptor-ligand interaction, intracellular signaling (iv) reduce fibrogenesis, inhibit matrix synthesis; and (v) resolve fibrosis by increasing scar matrix degradation, stimulating apoptosis of stellate cells, bone marrow (BM) or cell transplantation. The antifibrotic therapy may use drugs such as antioxidants, anti-inflammatory drugs, BM pro-genitor cells etc.

The following further describes an example of how the qFibrosis index may be used to determine the treatment plans for a patient having cirrhosis. Although cirrhosis is usually seen as a single fibrosis stage, in particular the end stage, there are in fact two types of cirrhosis, namely compensated cirrhosis and decompensated cirrhosis. It is not possible to differentiate between a tissue having compensated cirrhosis and a tissue having decompensated cirrhosis using prior art histological scoring systems as such systems view cirrhosis as a single fibrosis stage. On the other hand, the qFibrosis index is a quantitative index and is able to detect finer fibrosis progression. Thus, the qFibrosis index can be used for the diagnosis and differentiation of tissues with compensated and decompensated cirrhosis. Such differentiation is critical in deciding the treatment plans. This is because if the disease in the patient has progressed from compensated cirrhosis to decompensated cirrhosis, this means that the patient is at a much higher risk of dying and requires liver transplantation. Therefore, a method of treating a patient having cirrhosis may comprise performing liver transplant on the patient if an assessment of fibrosis in a tissue of the patient obtained using method 100 indicates that the patient has decompensated cirrhosis.

REFERENCES

1. R. Bataller and D. A. Brenner, "Liver fibrosis," *J. Clin. Invest.* 115(2), 209-218 (2005).
2. Friedman SL. "Liver fibrosis—from bench to bedside", *J. Hepatol.* 2003; 38 (Suppl. 1):S38-S53.
3. Castera, L., et al., *Prospective comparison of transient elastography, Fibrotest, APRI, and liver biopsy for the assessment of fibrosis in chronic hepatitis C.* Gastroenterology, 2005. 128 (2): p. 343-50.
4. Yin, M., et al., *Assessment of hepatic fibrosis with magnetic resonance elastography.* Clin Gastroenterol Hepatol, 2007. 5 (10): p. 1207-1213 e2.
5. Martinez S. M., *Noninvasive assessment of liver fibrosis.* Hepatology, 2011, 53(1):325-35.
6. Saadeh S., et al., *The role of liver biopsy in chronic hepatitis C.* Hepatology. 2001. 33(1):196-200

7. Bedossa P. and Carrat F., *Liver biopsy: the best, not the gold standard*. J Hepatol. 2009. 50(1):1-3
8. P. Bedossa, P. Bioulacsage, P. Callard, M. Chevallier, C. Degott, Y. Deugnier, M. Fabre, M. Reynes, J. J. Voigt, E. S. Zafrani, T. Poynard, and G. Babany, "*Intraobserver and interobserver variations in liver biopsy interpretation in patients with chronic hepatitis C. The French META-VIR Cooperative Study Group*", J. Hepatol 20(1), 15-20 (1994).
9. K. Gronbaek, P. B. Christensen, S. Hamilton-Dutoit, B. H. Federspiel, E. Hage, O. J. Jensen, and M. Vyberg, "*Interobserver variation in interpretation of serial liver biopsies from patients with chronic hepatitis C*", J. Viral Hepat. 9(6), 443-449 (2002).
10. Caballero T., et al., *Liver fibrosis assessment with semiquantitative indexes and image analysis quantification in sustained-responder and non-responder interferon-treated patients with chronic hepatitis C*. J. Hepatol 34 (2001) 740-747.
11. Goodman Z. D., et al., *Progression of fibrosis in advanced chronic hepatitis C: Evaluation by morphometric image analysis*. Hepatology, 2007, 45(4): 886-94.
12. Galvaruso V., et al., *Computer-assisted image analysis of liver collagen: relationship to Ishak scoring and hepatic venous pressure gradient*. Hepatology, 2009, 49(4): 1236-44.
13. Goodman Z. D., et al., *Fibrosis progression in chronic hepatitis C: morphometric image analysis in the HALT-C trial*. Hepatology, 2009, 50(6): 1738-49.
14. W. X. Sun, S. Chang, D. C. S. Tai, N. Tan, G. F. Xiao, H. H. Tang, and H. Yu, "*Non-linear optical microscopy: use of second harmonic generation and two photon microscopy for automated quantitative liver fibrosis studies,*" J. Biomed. Opt. 13(6), 064010 (2008).
15. Tai, D. C. S., et al. *Fibro-C-Index: comprehensive, morphology-based quantification of liver fibrosis using second harmonic generation and two-photon microscopy*. J. Biomed. Opt. 14(4), 044013 (2009).
16. Gailhouste, L., et al. *Fibrillar collagen scoring by second harmonic microscopy: A new tool in the assessment of liver fibrosis*. J. Hepatol 52(3), 398-406 (2010).
17. Zipfel W R, Williams R M, Webb W W. *Nonlinear magic: multiphoton microscopy in the biosciences*. Nat Biotechnol 2003; 21:1369-1377.
18. Campagnola P J, Millard A C, Terasaki M, Hoppe P E, Malone C J, Mohler W A. *Three-dimensional high-resolution second-harmonic generation imaging of endogenous structural proteins in biological tissues*. Biophys J 2002; 82:493-508.
19. Bedossa P., et al. *Sampling variability of liver fibrosis in chronic hepatitis C*. Hepatology 2003, 38(6):1449-57.
20. Goodman Z. D., *Grading and staging systems for inflammation and fibrosis in chronic liver diseases*. J. Hepatol 47(4), 598-607 (2007).
21. Standish R. A., *An appraisal of the histopathological assessment of liver fibrosis*. Gut. 2006, 55(4): 569-578.
22. Bedossa P., *Harmony in liver fibrosis . . .* , J. Hepatol 52(3), 313-4 (2010).
23. Ishak K, Baptista A, Bianchi L, et al. *Histological grading and staging of chronic hepatitis*. J Hepatol 1995; 22:696-9.
24. Bedossa, P. and T. Poynard, *An algorithm for the grading of activity in chronic hepatitis C. The METAVIR Cooperative Study Group*. Hepatology, 1996. 24 (2): p. 289-93.
25. Pinzani, M., *Liver fibrosis*. Springer Semin Immunopathol, 1999. 21 (4): p. 475-90.
26. Cholongitas E., et al. *A systematic review of the quality of liver biopsy specimens*. Am J Clin Pathol. 2006, 125 (5):710-21.
27. Colloredo G, Guido M, Sonzogni A, et al. *Impact of liver biopsy size on histological evaluation of chronic viral hepatitis: the smaller the sample, the milder the disease*. J Hepatol 2003; 39:239-44.
28. Kutami R, Girgrah N, Wanless I R, Sniderman K, Wong F S, Sherman M, et al. *The Laennec grading system for assessment of hepatic fibrosis: validation by correlation with wedged hepatic vein pressure and clinical features*. Hepatology 2000; 32:407A
29. Garcia-Tsao G., et al. *Now there are many (stages) where before there was one: In search of a pathophysiological classification of cirrhosis*. Hepatology, 2010, 51(4): 1445-9
30. Sethasine S., et al. *Quantitative histological-hemodynamic correlations in cirrhosis*. Hepatology, 2012, 55(4): 1146-53.
31. Chu C. J., Chang C C., Wang T F., Lee F Y., Chang F Y., Chen Y C., Chan C C., Huang H C., Wang S., Lee S D. *Detrimental effects of nitric oxide inhibition on hepatic encephalopathy in rats with thioacetamide-induced fulminant hepatic failure: Role of nitric oxide synthase isoforms*. Hepatology, 2006, 21, 1194-99.
32. MULLER A., MACHNIK F., ZIMMERMANN T., CHUBERT H. *Thioacetamide-induced irrhosislike liver lesions in rats—usefulness and reliability of this animal model*. Exp. Pathol., 1988, 34, 229-36.
33. AKAHOSHI T., HASHIZUME M., TANOUE K., SHIMABUKURO T., GOTOH N., OMIKAWA M., SUGIMACHI K. *Role of the spleen in liver fibrosis in rats may be mediated by transforming growth factor β-1*. J. Gastroentero.l Hepato.l, 2002, 17, 59-65.
34. CORBIN I R., MINUK G Y. *Serial Percutaneous Liver Biopsies in Laboratory Rats*. Dig. Dis. Sci., 2003, 48, 1939-43.
35. DEKEL R., ZVIBEL I., BRILL S., BRAZOVCKI E., HALPERN Z., OREN R. *Gliotoxin Ameliorates Development of Fibrosis and Cirrhosis in a Thioacetamide Rat Model*. Dig. Dis. Sci., 2003, 48, 1642-47.
36. L. Xu, M. I. Jordan, *On Convergence Properties of the EM Algorithm for Gaussian Mixture*, Neural Computation, 8, 1996, pp. 129-151.
37. Wu C. F. J. Jackknife, *bootstrap and other resampling methods in regression analysis*. Annals of Statistics 14 1261-1350, 1986
38. Guyon I, Weston J, Barhill S, Vapnik V. *Gene selection for cancer classification using support vector machines*. Mach. Learn., 46, 389-422, 2002
39. Abdi. H., & Williams, L. J. "*Principal component analysis*". Wiley Interdisciplinary Reviews: Computational Statistics, 2: 433-459, 2010.
40. W. H. Greene, "*Econometric Analysis*," Fifth edition, Prentice Hall, 720-723 (1993)
41. Franz Aurenhammer (1991). *Voronoi Diagrams—A Survey of a Fundamental Geometric Data Structure*. ACM Computing Surveys, 23(3):345-405, 1991
42. Abeel T, Helleputte T, Van de Peer Y, Dupont P and Saeys Y 2010 Robust biomarker identification for cancer diagnosis with ensemble feature selection methods *Bioinformatics* 26 392-8
43. Michal Cohen-Naftaly and Scott L. FriedMan Current status of novel antifibrotic therapies in patients with chronic liver disease *Therapeutic Advances in Gastroenterology* (2011) 4 (6) 391-417

What is claimed is:

1. A method for assessing fibrosis in a tissue using a test image which is an image of the tissue, wherein the test image comprises a plurality of pixels having respective intensity values and wherein the method comprises:
   (1a) automatically identifying, from the test image, a portal collagen area, a septal collagen area and a fibrillar collagen area respectively comprising pixels representing portal collagen, septal collagen and fibrillar collagen of the tissue, the fibrillar collagen including collagen in both pen-cellular and peri-sinusoidal spaces;
   (1b) obtaining quantitative values of one or more features for each identified area based on characteristics of the identified area in the test image; and
   (1c) assessing fibrosis using the quantitative values obtained for all the identified areas;
   wherein operation (1a) further comprises:
   (A) identifying, from the test image, collagen pixels and lumen pixels respectively comprising pixels representing collagen and lumens of the tissue; and
   (B) segmenting the collagen pixels into the portal collagen area, septal collagen area and fibrillar collagen area based on relations between the collagen pixels and the lumen pixels, comprising:
   (Bi) performing the following operations (i) and (ii) for each lumen area:
      (i) for each line of a plurality of lines, wherein each line extends from a center of the lumen area to a pixel not comprised in the lumen area and wherein the plurality of lines are spaced apart by predetermined angles from one another around the center of the lumen area, identifying collagen pixels overlapping with the line;
      (ii) extracting, based on the collagen pixels identified for all the lines, a sub-septal collagen area comprising pixels representing septal collagen in the tissue; and
   (Bii) segmenting the collagen pixels by identifying the septal collagen area as comprising the sub-septal collagen areas extracted for all the lumen areas;
   wherein prior to operation (Bii), the method further comprises:
      identifying collagen pixels not comprised in the sub-septal collagen areas and connected to the sub-septal collagen areas as further collagen pixels representing septal collagen in the tissue; and
      updating the sub-septal collagen areas to include said identified further collagen pixels representing septal collagen in the tissue.

2. The method according to claim 1, wherein the lumen pixels comprise multiple lumen areas, each having pixels representing a lumen in the tissue including boundary pixels, and wherein segmenting the collagen pixels further comprises:
   performing the following operations (3i) and (3ii) for each lumen area:
      (3i) for each distance in a plurality of distances, locating pixels at the distance from respective boundary pixels of the lumen area and determining the number of collagen pixels in said located pixels;
      (3ii) extracting, based on the number of collagen pixels determined for all the distances, a sub-portal collagen area comprising pixels representing portal collagen in the tissue; and
   segmenting the collagen pixels by identifying the portal collagen area as comprising the sub-portal collagen areas extracted for all the lumen areas.

3. The method according to claim 2, wherein extracting the sub-portal collagen area for each lumen area further comprises:
   for each distance, determining a collagen percentage as the percentage of the collagen pixels in said located pixels for the distance;
   calculating a cut-off distance as the distance at which the collagen percentage is at a predetermined proportion of the maximum collagen percentage determined; and
   identifying the collagen pixels in the pixels located for distances below the cut-off distance as the pixels of the sub-portal collagen area.

4. The method according to claim 3, wherein the predetermined proportion is between 40% to 60%.

5. The method according to claim 1 wherein extracting the sub-septal collagen area for each lumen area further comprises:
   for each line, determining a direction percentage as the percentage of collagen pixels within all pixels overlapping with the line;
   for each line, determining if the direction percentage determined for the line is larger than the direction percentages determined for its neighbouring lines and a predetermined percentage threshold; and
   if so, identifying the collagen pixels overlapping with the line as the pixels of the sub-septal collagen area.

6. The method according to claim 1, wherein operation (1b) further comprises:
   from each identified area, locating aggregated fiber pixels and distributed fiber pixels respectively representing aggregated fibers and distributed fibers of the tissue; and
   obtaining the quantitative values for each identified area using the aggregated fiber pixels and the distributed fiber pixels located from the identified area.

7. The method according to claim 6, wherein locating aggregated fiber pixels and distributed fiber pixels from each identified area further comprises:
   locating, from the identified area, a plurality of fibers, each comprising pixels representing a fiber of the tissue;
   identifying cross-link points in the identified area as pixels in more than one located fiber; and
   for each located fiber, determining if the fiber comprises at least one cross-link point and if so, locating the pixels comprised in the fiber as aggregated fiber pixels and if not, locating the pixels comprised in the fiber as distributed fiber pixels.

8. The method according to claim 7, wherein locating the plurality of fibers further comprises:
   identifying collagen segments from the identified area by segmenting the identified area into a plurality of connected components, each connected component being a collagen segment comprising a plurality of connected pixels;
   extracting, from each collagen segment, a skeleton having only pixels comprised in the plurality of fibers;
   identifying individual fibers in each skeleton based on characteristics of the pixels in the skeleton; and
   locating the plurality of fibers using the individual fibers in the skeletons.

9. The method according to claim 8, wherein extracting a skeleton from each collagen segment further comprises the following operations:

if the collagen segment comprises boundary pixels, generating an initial skeleton by removing the boundary pixels of the collagen segment; and if the initial skeleton comprises boundary pixels, repeatedly generating further skeletons by removing the boundary pixels of the most recently generated skeleton until the most recently generated skeleton does not comprise boundary pixels.

10. The method according to claim 8, wherein identifying individual fibers in each skeleton further comprises:

classifying each pixel in the skeleton based on whether the pixel represents an end of a fiber in the tissue, an intersection point between two or more fibers in the tissue or otherwise;

identifying the individual fibers in the skeleton using the classification of each pixel in the skeleton.

11. The method according to claim 10, wherein each pixel in the skeleton is classified as an end point if the pixel represents an end of a fiber, a branch point if the pixel represents an intersection between two or more fibers and a connect point otherwise, and wherein identifying the individual fibers comprises identifying each individual fiber by:

(14i) including an end point as a first pixel of the individual fiber;

(14ii) including successive adjacent connect points as further pixels of the individual fiber until a most recently included point is adjacent to an end point or a branch point; and (14iii) repeating operation (14ii) only if said most recently included point is adjacent to a branch point and there is a connect point adjacent to the branch point such that said connect point, the most recently included point and the branch point form a straight line.

12. The method according to claim 11, wherein identifying the individual fibers further comprises determining if there are any groups of connected pixels in the skeleton with at least one pixel not comprised in a previously identified individual fiber, and if so, identifying each of such groups as an individual fiber.

13. The method according to claim 8, wherein locating the plurality of fibers using the individual fibers in the skeletons further comprises:

determining if any pair of individual fibers is to be connected, and if so, connecting the pair of individual fibers to form a single individual fiber; and locating the plurality of fibers as the individual fibers;

wherein said determining if any pair of individual fibers is to be connected is based on:

(16i) orientations of the pixels in each individual fiber, (16ii) comparisons between the intensity values of a pixel in each individual fiber and of other pixels in the collagen segment, and (16iii) changes in the intensity values of pixels between the individual fibers.

14. The method according to claim 13, wherein for each individual fiber, the comparison between the intensity values of the pixel in the individual fiber and of other pixels in the collagen segment comprises:

a comparison between intensity values of said pixel of the individual fiber and of each direction from said pixel of the individual fiber, wherein each direction comprises pixels forming a straight line extending from said pixel of the individual fiber, with the lines spaced apart around said pixel of the individual fiber.

15. The method according to claim 1, wherein operation (1c) further comprises:

inputting the quantitative values into a trained model to obtain a plurality of probability values, each probability value indicating the probability that the tissue is at a particular stage of fibrosis; and calculating one or more indices using the plurality of probability values.

16. The method according to claim 15, wherein the trained model is obtained using a plurality of training images which are images of respective tissues with known stages of fibrosis and by:

(19a) identifying, from each training image, a portal collagen area, a septal collagen area and a fibrillar collagen area respectively comprising pixels representing portal collagen, septal collagen and fibrillar collagen of the respective tissue;

(19b) for each training image, obtaining quantitative values of one or more features for each identified area based on characteristics of the identified area in the training image; and (19c) training the model using the quantitative values obtained for all the training images.

17. The method according to claim 16, wherein operation (19b) comprises:

for each training image, obtaining quantitative values of initial portal collagen features for the portal collagen area, quantitative values of initial septal collagen features for the septal collagen area and quantitative values of initial fibrillar collagen features for the fibrillar collagen area; and based on the quantitative values obtained for all the training images, selecting relevant portal collagen features, relevant septal collagen features and relevant fibrillar collagen features respectively from the initial portal collagen features, initial septal collagen features and initial fibrillar collagen features; and wherein the quantitative values used in operations (1c) and (19c) are quantitative values of the relevant portal collagen features, relevant septal collagen features and relevant fibrillar collagen features selected in operation (19b).

18. The method according to claim 16, wherein prior to using the quantitative values in operations (1c) and (19c), the quantitative values for each identified area are converted into a plurality of un-correlated components.

19. The method according to claim 18, wherein the quantitative values for each identified area are converted into a plurality of un-correlated components by:

transforming the quantitative values for the identified area into principal components via principal component analysis; and selecting a subset of the principal components as the plurality of un-correlated components for the identified area.

20. The method according to claim 1, wherein the one or more features whose quantitative values are obtained in operation (1b) comprises one or more of:

a ratio between the number of pixels in the portal collagen area to the total number of pixels in all the identified areas;

a ratio between the number of pixels in the septal collagen area to the total number of pixels in all the identified areas;

a ratio between the number of pixels in the fibrillar collagen area to the total number of pixels in all the identified areas;

an average thickness of the portal collagen area; and an average thickness of the septal collagen area.

21. The method according to claim 1, wherein the test image is obtained by imaging a biopsy tissue sample extracted from the tissue without staining the biopsy tissue sample.

22. The method according to claim 1, wherein the tissue is a liver tissue.

23. The method according to claim 1, wherein the method is used for one or more of the following:
(26i) assisting pathologists in assessing fibrosis in tissues;
(26ii) educating inexperienced pathologists on how to assess fibrosis in tissues;
(26iii) evaluating effects of a particular treatment on a patient;
(26iv) diagnosing a level of fibrosis in a tissue; and
(26v) validating diagnosis tools for assessing fibrosis in a tissue.

24. A computer system for assessing fibrosis in a tissue using a test image which is an image of the tissue, wherein the test image comprises a plurality of pixels having respective intensity values,
the computer system having a processor arranged to implement program instructions, wherein upon implementing the program instructions the processor is operative to
(1a) automatically identify, from the test image, a portal collagen area, a septal collagen area and a fibrillar collagen area respectively comprising pixels representing portal collagen, septal collagen and fibrillar collagen of the tissue, the fibrillar collagen including collagen in both peri-cellular and peri-sinusoidal spaces;
(1b) obtain quantitative values of one or more features for each identified area based on characteristics of the identified area in the test image; and
(1c) assess fibrosis using the quantitative values obtained for all the identified areas
wherein operation (1a) further comprises:
(A) identifying, from the test image, collagen pixels and lumen pixels respectively comprising pixels representing collagen and lumens of the tissue; and
(B) segmenting the collagen pixels into the portal collagen area, septal collagen area and fibrillar collagen area based on relations between the collagen pixels and the lumen pixels, comprising:
(Bi) performing the following operations (i) and (ii) for each lumen area:
(i) for each line of a plurality of lines, wherein each line extends from a center of the lumen area to a pixel not comprised in the lumen area and wherein the plurality of lines are spaced apart by predetermined angles from one another around the center of the lumen area, identifying collagen pixels overlapping with the line;
(ii) extracting, based on the collagen pixels identified for all the lines, a sub-septal collagen area comprising pixels representing septal collagen in the tissue; and
(Bii) segmenting the collagen pixels by identifying the septal collagen area as comprising the sub-septal collagen areas extracted for all the lumen areas;
wherein the processor is operative to, prior to operation (Bii):
identify collagen pixels not comprised in the sub-septal collagen areas and connected to the sub-septal collagen areas as further collagen pixels representing septal collagen in the tissue; and
update the sub-septal collagen areas to include said identified further collagen pixels representing septal collagen in the tissue.

25. A non-transitory computer-readable medium containing instructions operable by a processor of a computer system to cause the processor to assess fibrosis in a tissue using a test image which is an image of the tissue, wherein the test image comprises a plurality of pixels having respective intensity values and wherein the assessment comprises:
(1a) automatically identifying, from the test image, a portal collagen area, a septal collagen area and a fibrillar collagen area respectively comprising pixels representing portal collagen, septal collagen and fibrillar collagen of the tissue, the fibrillar collagen including collagen in both peri-cellular and peri-sinusoidal spaces;
(1b) obtaining quantitative values of one or more features for each identified area based on characteristics of the identified area in the test image; and
(1c) assessing fibrosis using the quantitative values obtained for all the identified areas,
wherein operation (1a) further comprises:
(A) identifying, from the test image, collagen pixels and lumen pixels respectively comprising pixels representing collagen and lumens of the tissue; and
(B) segmenting the collagen pixels into the portal collagen area, septal collagen area and fibrillar collagen area based on relations between the collagen pixels and the lumen pixels, comprising:
(Bi) performing the following operations (i) and (ii) for each lumen area:
(i) for each line of a plurality of lines, wherein each line extends from a center of the lumen area to a pixel not comprised in the lumen area and wherein the plurality of lines are spaced apart by predetermined angles from one another around the center of the lumen area, identifying collagen pixels overlapping with the line;
(ii) extracting, based on the collagen pixels identified for all the lines, a sub-septal collagen area comprising pixels representing septal collagen in the tissue; and
(Bii) segmenting the collagen pixels by identifying the septal collagen area as comprising the sub-septal collagen areas extracted for all the lumen areas;
wherein the instructions are operative by the processor to cause the processor to, prior to operation (Bii):
identify collagen pixels not comprised in the sub-septal collagen areas and connected to the sub-septal collagen areas as further collagen pixels representing septal collagen in the tissue; and
update the sub-septal collagen areas to include said identified further collagen pixels representing septal collagen in the tissue.

26. A computer system according to claim 24 which is a cloud computing system and the processor is located within a server remote from a user of the system.

* * * * *